(12) United States Patent
Kobayashi

(10) Patent No.: US 7,881,774 B2
(45) Date of Patent: Feb. 1, 2011

(54) APPARATUS FOR OBTAINING ULTRASONIC IMAGE AND METHOD OF OBTAINING ULTRASONIC IMAGE

(75) Inventor: Tadaharu Kobayashi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 637 days.

(21) Appl. No.: 11/458,233

(22) Filed: Jul. 18, 2006

(65) Prior Publication Data
US 2007/0038103 A1 Feb. 15, 2007

(30) Foreign Application Priority Data
Jul. 19, 2005 (JP) ............................. 2005-208275

(51) Int. Cl.
*A61B 5/05* (2006.01)
(52) U.S. Cl. ....................................................... 600/428
(58) Field of Classification Search ................. 600/428, 600/407, 413, 437
See application file for complete search history.

(56) References Cited

U.S. PATENT DOCUMENTS

| 6,544,175 | B1 | 4/2003 | Newman | |
|---|---|---|---|---|
| 7,103,400 | B2 * | 9/2006 | Ossmann et al. | 600/428 |
| 2004/0215077 | A1 | 10/2004 | Witt et al. | |

* cited by examiner

*Primary Examiner*—Brian Casler
*Assistant Examiner*—Elmer Chao
(74) *Attorney, Agent, or Firm*—Oblon, Spivak, McClelland, Maier & Neustadt, L.L.P.

(57) ABSTRACT

A transmitting/receiving circuit drives an ultrasonic probe in accordance with a trigger signal based on an electrocardiographic waveform under the control of a control device so as to scan a plurality of regions, and obtains scan data for each region. During the scanning, the circuit causes the probe to scan the respective regions so that scan data in which time phases of the electrocardiographic waveform substantially coincide are obtained in the vicinities of the boundary between at least two adjacent regions among the regions. That is, in adjacent regions, the circuit causes the probe to scan the respective regions in the main or sub-scanning directions set to be reverse to each other. Further, an image processor generates ultrasonic image data of the range in which the regions are joined, on the basis of the scan data obtained by starting scanning at the same time phase.

22 Claims, 13 Drawing Sheets

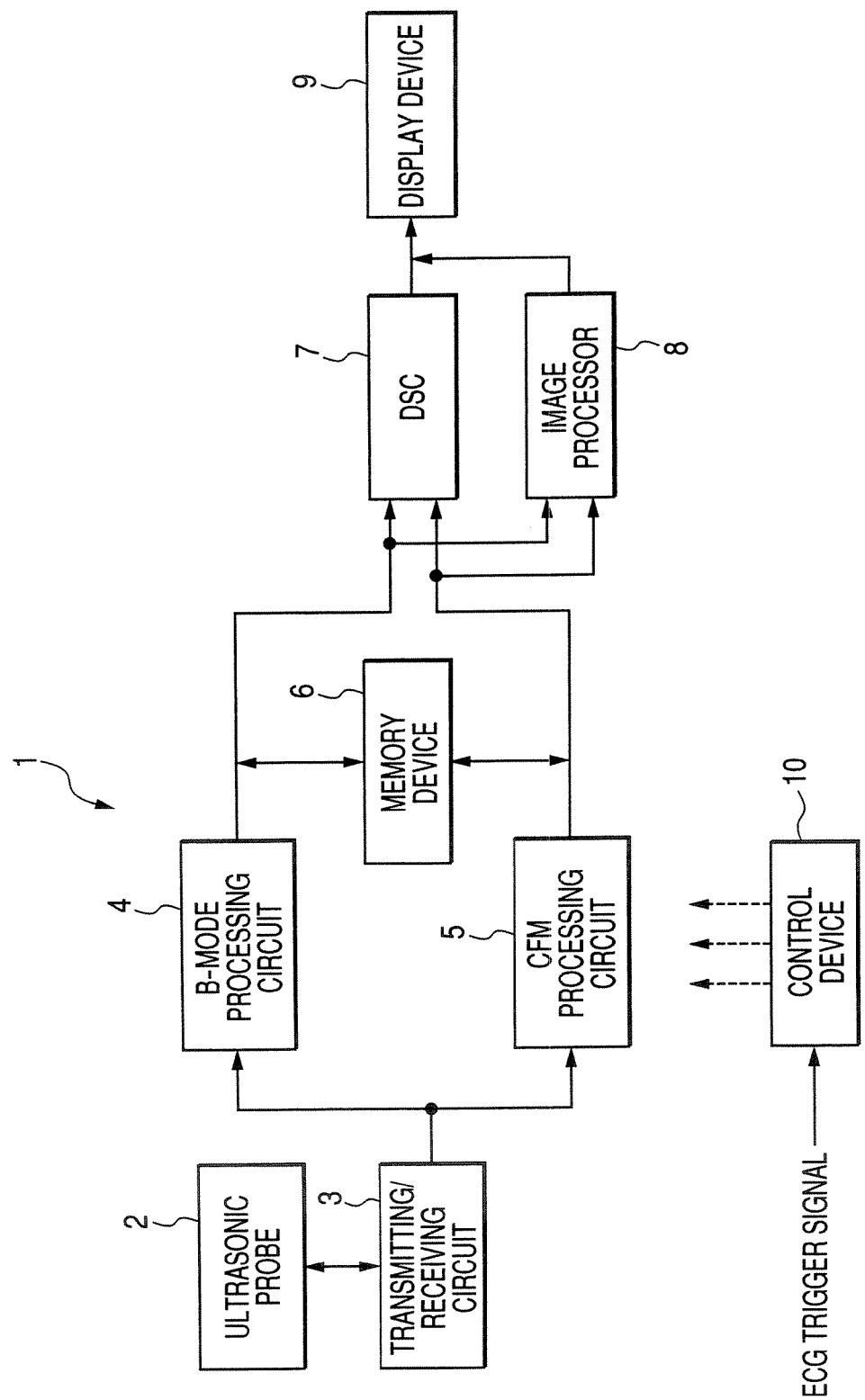

APPARATUS FOR OBTAINING ULTRASONIC IMAGE AND METHOD OF OBTAINING ULTRASONIC IMAGE

BACKGROUND OF THE INVENTION

1. Field of the Invention

The present invention relates to an apparatus for obtaining an ultrasonic image, which three-dimensionally transmits an ultrasonic wave into a subject and receives the reflected wave from the subject, thereby obtaining diagnosis information within the subject, and more particularly, to an apparatus for obtaining an ultrasonic image, which performs scanning by using an electrocardiographic signal (ECG signal).

2. Description of the Related Art

Recently, a so-called two-dimensional ultrasonic probe is being developed, in which ultrasonic transducers are two-dimensionally arranged so as to three-dimensionally transmit and receive an ultrasonic beam into and from a subject.

As shown in FIG. 1, an apparatus for obtaining an ultrasonic image, provided with the two-dimensional ultrasonic probe, can transmit and receive an ultrasonic beam three-dimensionally. Therefore, the apparatus can scan the entire region of a region of interest (ROI) in a short time in comparison with an apparatus for obtaining an ultrasonic image, which is provided with a one-dimensional ultrasonic probe having ultrasonic transducers arranged one-dimensionally. Particularly, the availability thereof is noticeable in circulatory organs in which a heartbeat is present.

The volume data obtained by three-dimensionally scanning is subjected to image processing, such as volume rendering (hereinafter, referred to as 'VR processing') or MPR (Multiplannar Reconstruction) processing. Then, three-dimensional image data or image data in an arbitrary cross-section is generated.

However, when scanning is performed by the two-dimensional ultrasonic probe, an amount of data generated per unit of time rapidly increases, compared with when scanning is performed by the one-dimensional ultrasonic probe. For example, when scanning a wide range of 60°×60°, the two-dimensional ultrasonic probe needs to be provided with a beam former, of which the parallel simultaneous reception number of ultrasonic beam (reception beam) is about 16. Accordingly, such a hardware is needed, that can process data generated by the parallel simultaneous reception number of about 16. Such enlargement of hardware significantly increases a cost of the apparatus for obtaining an ultrasonic image, which becomes a large obstacle to spread of the apparatus.

In the conventional apparatus for obtaining an ultrasonic image, a hardware of which the parallel simultaneous reception number of ultrasonic beam (reception beam) is about four is adopted to improve the ratio of cost to effect. Therefore, in order to obtain an image having a quality available for diagnosis without damaging a real-time property, a scanning range S shown in FIG. 1 needs to be narrowed into a scanning range S shown in FIG. 2, when the scanning is performed by using the apparatus for obtaining an ultrasonic image.

As a method of overcoming a constraint of transmission and reception caused by the scale of hardware, a method has been proposed, in which the entire scanning range S is divided into a plurality of regions to perform scanning (refer to U.S. Pat. No. 6,544,175). Hereinafter, the method will be described with reference to FIGS. 3A and 3B.

As shown in FIG. 3A, the apparatus for obtaining an ultrasonic image according to the related art divides the entire scanning range S into a plurality of regions. In the example shown in FIG. 3A, the apparatus for obtaining an ultrasonic image according to the related art divides the entire scanning range S into four regions A to D. Hereinafter, the respective divided regions A to D are referred to as sub-volumes. In the example shown in FIG. 3A, four sub-volumes are respectively set to sub-volumes A to D. The apparatus for obtaining an ultrasonic image according to the related art divides the entire scanning range S, so that the sub-volumes A to D are lined up in order of A to D. Further, the apparatus for obtaining an ultrasonic image, of which the parallel simultaneous reception number of ultrasonic beam (reception beam) is small, scans an ultrasonic beam by the sub-volume, as shown in FIG. 3B.

The scanning of the respective sub-volumes, performed by the apparatus for obtaining an ultrasonic image according to the related art, will be described with reference to FIGS. 4A to 4D. FIG. 4A is a schematic view showing a scanning range of the apparatus for obtaining an ultrasonic image according to the related art. FIGS. 4B to 4D are schematic views illustrating the scanning range and scanning direction of the apparatus for obtaining an ultrasonic image according to the related art, and are diagrams (top views) seen from the ultrasonic probe.

As shown in FIGS. 4A and 4B, the apparatus for obtaining an ultrasonic image according to the related art scans an ultrasonic beam in a main scanning direction X and scans an ultrasonic beam in a sub-scanning direction Y orthogonal to the main scanning direction X, thereby scanning the entire range of the sub-volume A. Further, the apparatus for obtaining an ultrasonic image according to the related art scans the sub-volume A several times during one heartbeat and scans the sub-volume B at the next heartbeat. Similarly, the apparatus for obtaining an ultrasonic image scans the sub-volumes C and D.

FIGS. 4C and 4D show the sub-scanning direction in the sub-volumes A and B. As shown in FIG. 4C, the apparatus for obtaining an ultrasonic image according to the related art scans an ultrasonic beam in the sub-scanning direction Y (from the left side to the right side in the drawing), thereby scanning the sub-volume A. In the sub-volume A, the apparatus for obtaining an ultrasonic image according to the related art scans an ultrasonic beam toward the boundary with the sub-volume B.

As shown in FIG. 4D, the apparatus for obtaining an ultrasonic image according to the related art scans an ultrasonic beam in the same sub-scanning direction Y (from the left side to the right side in the drawing) as the sub-volume A, thereby scanning the sub-volume B. In the sub-volume B, the apparatus for obtaining an ultrasonic image according to the related art starts scanning from the boundary with the sub-volume A so as to scan an ultrasonic beam toward the boundary with the sub-volume C.

On the sub-volumes C and D, the apparatus for obtaining an ultrasonic image according to the related art also scans an ultrasonic beam in the sub-scanning direction Y (from the left side to the right side in the drawing), thereby scanning the sub-volumes C and D. Further, the apparatus for obtaining an ultrasonic image according to the related art combines the scan data obtained by scanning the respective sub-volumes so as to generate the scan data of the entire scanning range.

However, since the apparatus for obtaining an ultrasonic image according to the related art scans an ultrasonic beam in the same sub-scanning direction in the respective sub-volumes, the following problem occurs. The problem will be described with reference to FIG. 5. FIG. 5 is a schematic view illustrating the scanning range and scanning direction of the apparatus for obtaining an ultrasonic image according to the related art, and is a diagram (top view) seen from the ultrasonic probe.

The apparatus for obtaining an ultrasonic image according to the related art combines scan data, obtained at a different heartbeat and obtained at the same time phase, so as to generate one volume data corresponding to the entire scanning range.

For example, the apparatus for obtaining an ultrasonic image according to the related art scans the sub-volumes A to D between time phases $t_0$ and $t_1$ so as to obtain scan data $A_0$ to $D_0$. Then, the apparatus combines the scan data $A_0$ to $D_0$ so as to generate the scan data of the entire range of a region of interest between the time phases $t_0$ and $t_1$.

FIG. 5 shows a portion of the scan data generated in such a manner. For a simple explanation, only the scan data $A_0$ and $B_0$ are shown in FIG. 5. On both the sub-volumes A and B, the apparatus scans an ultrasonic beam in the same scanning directions (the main scanning direction X and the sub-scanning direction Y), thereby obtaining the scan data $A_0$ and $B_0$.

Here, attention is paid to the vicinity of the boundary L between the sub-volumes A and B. In the sub-volume A, one line of scan data obtained in a scanning range (the vicinity of the boundary L with the sub-volume B) of the right end thereof is data obtained between time phases $(t_1-\delta t)$ and $t_1$. Meanwhile, in the sub-volume B, one line of scan data obtained in a scanning range (the vicinity of the boundary L with the sub-volume A) of the left end thereof is data obtained between time phases $t_0$ and $(t_1+\delta t)$. Here, $\delta t$ means a time which is required for scanning one line at the time of radiating an ultrasonic beam in the main scanning direction X. Accordingly, in the vicinities of the boundary L between the sub-volumes A and B, a difference of about $\Delta t$ is present in the time phases where the scan data are obtained.

For example, when the sub-volume is scanned 20 times during one heartbeat and a time of one heartbeat is set to one second, a scanning time $\Delta t$ required for performing scanning one time becomes 0.05 second ($\Delta t=1/20$). Therefore, in the vicinities of the boundary L between the sub-volumes A and B, the time phase difference of about 0.05 second occurs. That is, in the vicinities of the boundary L between the sub-volumes A and B, the scan data are obtained at different time phases ($\Delta t=0.05$).

The time phase difference (about 0.05 second) is such a value that cannot be ignored in a portion, such as a valve or core wall of the heart, in which the motion is severe. When the scanning according to the related art is performed on a part, in which the motion is severe, so as to generate a three-dimensional image or MPR image based on the scan data obtained by the scanning, a streaky artifact is generated in a position corresponding to the boundary between the respective sub-volumes.

The artifact will be described with reference to FIGS. 6A and 6B. FIG. 6A is a schematic view showing a scanning range of the apparatus for obtaining an ultrasonic image according to the related art. FIG. 6B is a diagram showing an image obtained by the scanning performed by the apparatus for obtaining an ultrasonic image according to the related art.

As shown in FIG. 6A, the apparatus for obtaining an ultrasonic image according to the related art divides a scanning range into sub-volumes A to D, the scanning range including a diagnosis portion 100 such as the heart. Then, the apparatus scans the respective sub-volumes. Further, the apparatus for obtaining an ultrasonic image according to the related art combines the scan data obtained at the same time phase so as to generate a three-dimensional image or MPR image through the volume rendering or MPR processing.

FIG. 6B shows an image obtained by performing the rendering process on the obtained scan data, in a state where an observation direction P shown in FIG. 6A is set to a direction of line of sight. As described above, the time phase difference occurs in the vicinities of the boundary between the sub-volumes. Therefore, in an image 101 of the diagnosis portion 100, a vertically-running streaky artifact 102 is generated in a position corresponding to the boundary between the sub-volumes.

SUMMARY OF THE INVENTION

An object of the invention is to provide an apparatus for obtaining an ultrasonic image, which scans a plurality of regions in accordance with a trigger signal based on an electrocardiographic waveform, capable of reducing a difference in time phases when scan data are obtained, and a method of obtaining an ultrasonic image.

According to an aspect of the invention, an apparatus for obtaining an ultrasonic image includes an ultrasonic probe that scans an ultrasonic beam in a main scanning direction and a sub-scanning direction, a scan device that receives a trigger signal based on an electrocardiographic waveform, drives the ultrasonic probe in accordance with the trigger signal so as to scan a plurality of regions, and obtains scan data for each region, and an image generating device that combines the scan data obtained for each region so as to generate ultrasonic image data of the range in which the plurality of regions are joined. The scan device causes the ultrasonic probe to scan the respective regions, so that scan data in which time phases of the electrocardiographic waveform substantially coincide are obtained in the vicinities of the boundary between at least two adjacent regions among the plurality of regions.

In the vicinities of the boundary between the regions adjacent to each other, the scan data in which the time phases of the electrocardiographic waveform substantially coincide are obtained. Therefore, a difference in the time phases where the scan data are obtained can be reduced in the vicinities of the boundary. Accordingly, it is possible to suppress an artifact from being generated, the artifact being generated in a position corresponding to the boundary between the respective regions in the ultrasonic image.

According to another aspect of the invention, an apparatus for obtaining an ultrasonic image includes an ultrasonic probe that scans an ultrasonic beam in a main scanning direction and a sub-scanning direction, a scan device that receives a trigger signal based on an electrocardiographic waveform, drives the ultrasonic probe in accordance with the trigger signal so as to scan a plurality of regions, and obtains scan data for each region, and an image generating device that combines the scan data obtained for each region so as to generate ultrasonic image data of the range in which the plurality of regions are joined. In adjacent regions, the scan device causes the ultrasonic probe to scan the respective regions with the main or sub-scanning directions set to be reverse to each other, thereby obtaining scan data.

In adjacent regions, the ultrasonic probe scans an ultrasonic beam, with the main or sub-scanning directions set to be reverse to each other. Therefore, the scan data in which the time phases of the electrocardiographic waveform substantially coincide are obtained in the vicinities of the boundary between adjacent regions. Accordingly, a difference in the time phases where the scan data are obtained can be reduced in the vicinities of the boundary. As a result, it is possible to suppress an artifact from being generated, the artifact being generated in a position corresponding to the boundary between the respective regions in the ultrasonic image.

BRIEF DESCRIPTION OF THE DRAWINGS

FIG. 7 is a block diagram showing a schematic construction of an apparatus for obtaining an ultrasonic image according to an embodiment of the invention;

DESCRIPTION OF THE PREFERRED EMBODIMENTS

Figure 1:
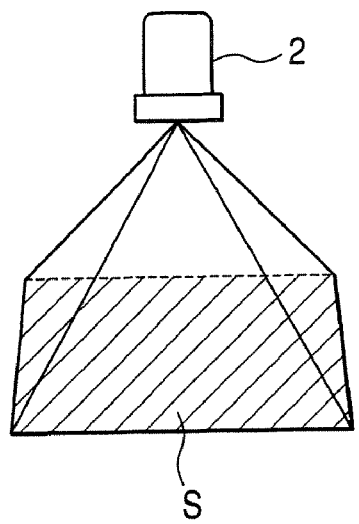
FIG. 1 is a schematic view illustrating a scanning range of an apparatus for obtaining an ultrasonic image according to the related art.
Figure 2:
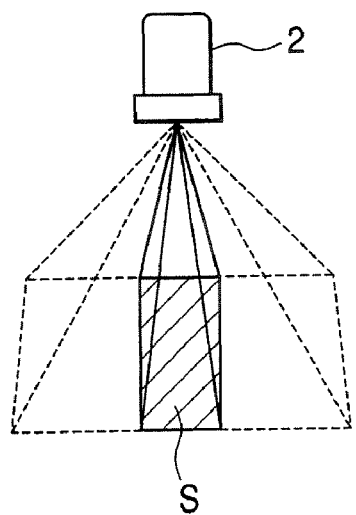
FIG. 2 is a schematic view illustrating a scanning range of the apparatus for obtaining an ultrasonic image according to the related art.

An apparatus for obtaining an ultrasonic image and a method of obtaining an ultrasonic image according to an embodiment of the invention will be described. First, the construction of the apparatus for obtaining an ultrasonic image according to the present embodiment will be described with reference to FIG. 7. FIG. 7 is a block diagram schematically showing the construction of the apparatus for obtaining an ultrasonic image according to the embodiment of the invention.

An ultrasonic probe 2 is composed of a two-dimensional ultrasonic probe having ultrasonic transducers arranged in a matrix shape. The ultrasonic probe 2 three-dimensionally transmits an ultrasonic wave and receives three-dimensional data, which have shapes radially broadening from the probe surface, as an echo signal.

The ultrasonic probe 2 used in the apparatus 1 for obtaining an ultrasonic image is not limited to the two-dimensional ultrasonic probe, and may be a one-dimensional ultrasonic probe. For example, in a state where a one-dimensional ultrasonic probe having ultrasonic transducers arranged in a scanning direction is connected to the apparatus 1 for obtaining an ultrasonic image, three-dimensional data may be obtained by mechanically rocking the ultrasonic transducers in the direction orthogonal to the scanning direction.

A transmitting/receiving circuit 3, which is composed of a transmitting section and receiving section, supplies an electrical signal to the ultrasonic probe 2 so as to generate an ultrasonic wave, and receives the echo signal received by the ultrasonic probe 2.

The transmitting section within the transmitting/receiving circuit 3 includes a clock generating circuit, a transmission delay circuit, and a pulsar circuit, which are not shown. The clock generating circuit generates a clock signal for determining the transmission timing and transmission frequency of an ultrasonic wave signal. The transmission delay circuit is a circuit for delaying an ultrasonic wave so as to adjust a transmission focus during the transmission of an ultrasonic wave. The pulsar circuit, in which several minutes of pulsar of individual channels corresponding to the respective ultrasonic transducers are built-in, generates a driving pulse at the delayed transmission timing so as to supply the driving pulse to the respective ultrasonic transducers of the ultrasonic probe 2.

The transmitting section of the transmitting/receiving circuit 3 supplies an electrical signal to the ultrasonic probe 2 in accordance with the control signal output from a control device 10 so as to generate an ultrasonic beam, thereby scanning a predetermined range. The control signal includes information indicating a scanning range, a main scanning direction, and a sub-scanning direction of the ultrasonic probe 2. The transmitting section drives the ultrasonic probe in accordance with the information.

For example, the transmitting section of the transmitting/receiving circuit 3 receives a control signal from the control device 10. The control signal includes information on a division pattern, which is used to divide a desired scanning range into a plurality of regions, and the main and sub-scanning directions in the respective divided regions. In accordance with the control signal, the transmitting section divides a scanning range into a plurality of ranges and causes the ultrasonic probe 2 to scan the respective regions by changing the main and sub-scanning directions for each region.

The receiving section of the transmitting/receiving circuit 3 includes a preamplifier circuit, an A/D conversion circuit, and a reception delay/adder circuit, which are not shown. The preamplifier circuit amplifies an echo signal, which is output from each of the ultrasonic transducers of the ultrasonic probe 2, for each transmission channel. The A/D conversion circuit A/D-converts the amplified echo signal. The reception delay/adder circuit imparts and adds a delay time, which is necessary for determining the reception directivity with respect to the A/D-converted echo signal. By adding a delay time, a reflected component from the direction according to the reception directivity is emphasized. Further, the signal added by the transmitting/receiving circuit 3 is referred to as 'RF data'.

The RF data output from the transmitting/receiving circuit 3 is output to a B-mode processing circuit 4 or a CFM processing circuit 5 in accordance with the purpose.

The B-mode processing circuit 4 visualizes the amplitude information of an echo signal, and generates B-mode raster data from the echo signal. Specifically, the B-mode processing circuit 4 performs band-pass filter processing on the RF data. After that, the B-mode processing circuit detects the envelope curve of the output signal, and compresses the detected data through logarithmic conversion. The data generated by the B-mode processing circuit is referred to as B-mode raster data.

The CFM processing circuit 5 visualizes information on running blood flow and generates color raster data. The blood flow information includes information such as rate, dispersion, power and the like, and is obtained as binarized information. Specifically, the CFM processing circuit 5 includes an MTI filter, an autocorrelator, and a flow rate/dispersion calculator. The CFM processing circuit 5 performs high-pass filter processing (MTI filter processing) for separating tissue signals and blood flow signals so as to seek blood flow information such as the transfer rate, dispersion, and power of blood flow through the autocorrelation.

A memory device 6 is composed of memory, and temporarily stores and holds the raster data generated by the B-mode processing circuit 4 and the CFM processing circuit 5.

A digital scan converter (DSC) 7 converts the raster data into data represented by orthogonal coordinates, in order to obtain an image represented by orthogonal coordinates. The DSC 7 reads the signal-processed raster data, represented by a signal array of scanning lines, from the memory device 6 so as to convert the read signal-processed raster data into coordinate data based on spatial information (scan conversion processing). For example, the DSC 7 generates two-dimensional cross-sectional image data on the basis of the B mode raster data, and outputs the image data to a display device 9.

An image processor 8 is composed of an ASIC, FPGA, or CPU, which is built in the apparatus 1 for obtaining an ultrasonic image, or is composed of a workstation which is provided outside the apparatus 1 for obtaining an ultrasonic image. When a two-dimensional probe is connected to the apparatus 1 for obtaining an ultrasonic image, the image processor 8 reads the raster data from the memory device 6, generates three-dimensional image data or MPR image data (arbitrary cross-sectional image data) through rendering or MRP processing, and outputs the image data to the display device 9. The image processor 8 corresponds to 'an image generating device' of the invention.

The display device 9 is composed of a monitor such as CRT or liquid crystal display and displays a cross-sectional image, a three-dimensional image or blood flow information on the monitor screen.

The control device 10 is connected to the respective sections of the apparatus 1 for obtaining an ultrasonic image, and controls the respective sections of the apparatus 1 for obtaining an ultrasonic image. The control device 10 is composed of a CPU or the like and executes a control program of the apparatus for obtaining an ultrasonic image, which is stored in a memory such as ROM (not shown), so as to control the respective sections. The memory such as ROM stores the control program and various setting conditions of the apparatus for obtaining an ultrasonic image.

In the present embodiment, an electrocardiographic waveform (ECG signal) of a subject is obtained by using an electrocardiograph. Further, the control device 10 receives an ECG trigger signal from the outside of the apparatus 1 for obtaining an ultrasonic image, and outputs a control signal to the transmitting/receiving circuit 3 in accordance with the ECG trigger signal. For example, the control device 10 is provided with a signal generator for generating an ECG trigger signal when an R wave is detected by an electrocardiograph. The signal generator outputs an ECG trigger signal to the control device 10 when an R wave is detected by the electrocardiograph. When receiving the ECG trigger signal, the control device 10 outputs a control signal to the transmitting/receiving circuit 3. The transmitting/receiving circuit 3 drives the ultrasonic probe 2 in accordance with the control signal so as to scan a predetermined range. As such, the scanning begins in accordance with the ECG trigger signal.

Further, an electrocardiographic waveform (ECG signal) may be input to the control device 10, so that the control device 10 detects an R wave. In this case, the control device 10 outputs a control signal to the transmitting/receiving circuit 3, when detecting an R wave. The control signal, which is output to the transmitting/receiving circuit 3 by the control device 10, includes a scanning range of an ultrasonic beam and the main and sub-scanning directions of the ultrasonic beam.

The memory (not shown) such as ROM, connected to the control device 10, stores information on a division pattern of the scanning range and the main and sub-scanning directions in the respective divided regions. The division pattern, the main scanning direction, and sub-scanning direction are previously set information, and the descriptions thereof will be made in detail when the operation of the apparatus 1 for obtaining an ultrasonic image is described.

When receiving information indicating a range to be scanned (a desired scanning range), the control device 10 divides the desired scanning range through a predetermined method (a predetermined division pattern). Further, the control device 10 determines the main and sub-scanning directions for each of the divided regions (sub-volumes). For example, the control device 10 reads the information, such as the division pattern and the main and sub-scanning directions in each divided region, from the memory so as to divide a desired scanning range. Further, the control device 10 outputs the control signal to the transmitting/receiving circuit 3. The control signal includes the information indicating the division pattern and the main and sub-scanning directions of each region. The transmitting/receiving circuit 3 causes the ultrasonic probe 2 to scan the respective divided regions in accordance with the control signal including the division pattern.

The apparatus 1 for obtaining an ultrasonic image is further provided with an operating section (not shown) for inputting various settings which are related to a transmission and reception condition of ultrasonic wave. The operating section includes a pointing device, such as a joy stick or a track ball, a switch, various buttons, a keyboard, a touch command screen (TCS) or the like. The information input by the operating section is transmitted to the control device 10, and the control device 10 controls the respective sections of the apparatus 1 for obtaining an ultrasonic image in accordance with the information.

The transmitting/receiving circuit 3 and the control device 10 correspond to 'a scan device' of the invention.

(Operation)

Figure 8:
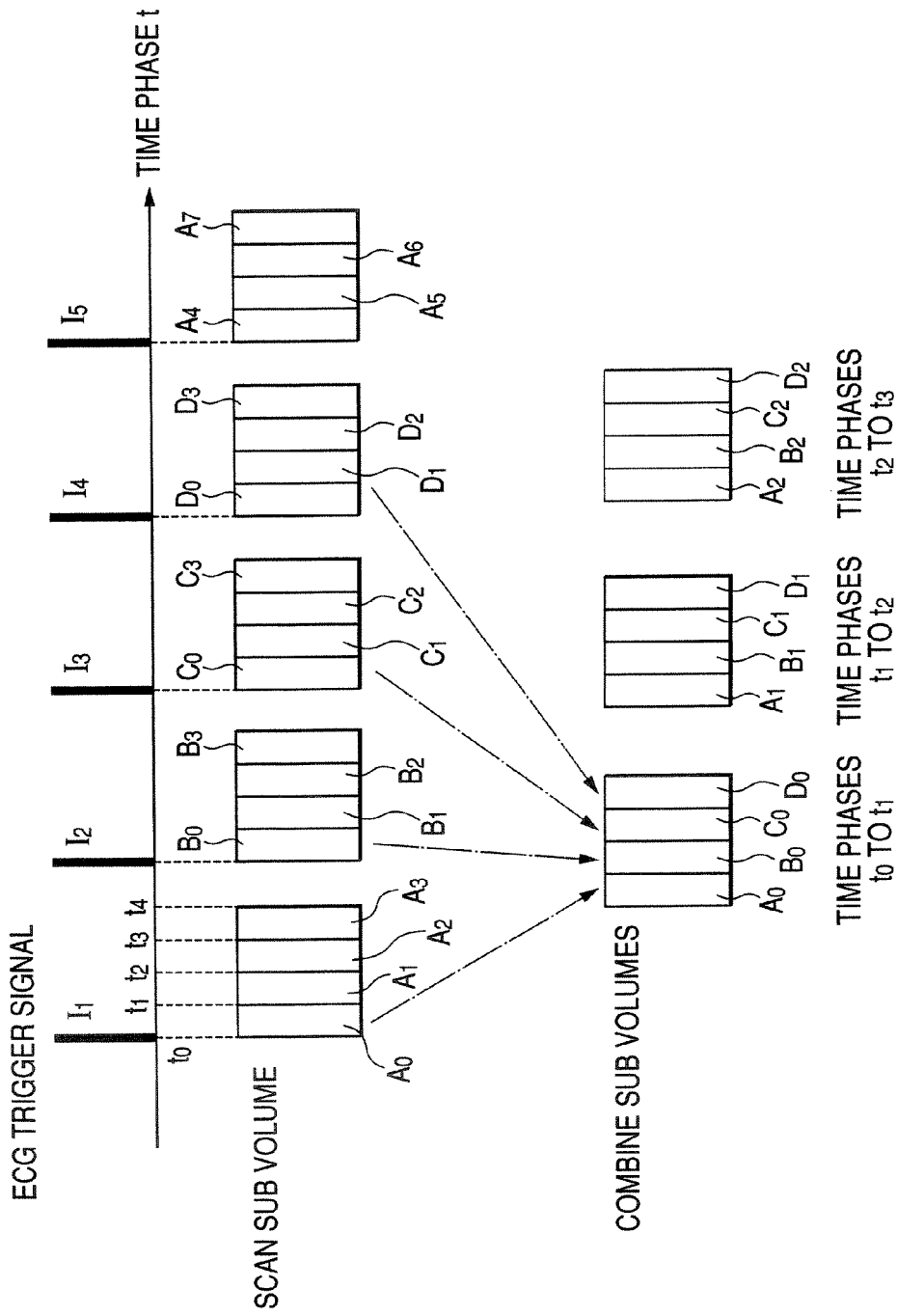
FIG. 8 is a schematic view illustrating scan data obtained at each time phase and a process of synthesizing the scan data.

The detailed operation of the apparatus 1 for obtaining an ultrasonic image according to the present embodiment will be described. The apparatus 1 for obtaining an ultrasonic image scans the entire scanning range by the sub-volume, using an ECG trigger signal. First, a scanning range of the apparatus 1 for obtaining an ultrasonic image according to the present embodiment, and the scanning timing thereof will be described with reference to FIGS. 3A, 3B, and 8. FIG. 8 is a schematic view illustrating scan data obtained at each time phase and a process of synthesizing the scan data.

Figure 3A:
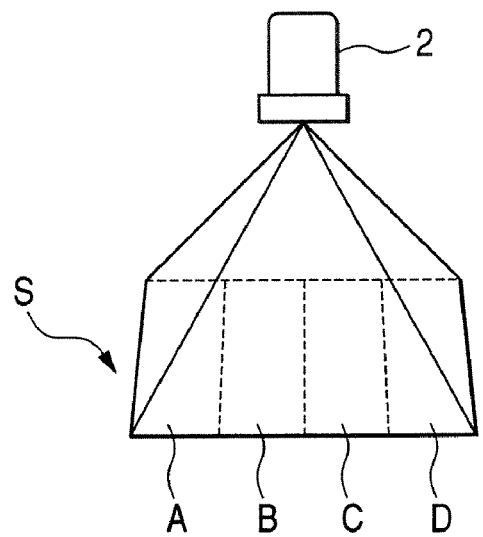
FIGS. 3A and 3B are schematic views illustrating a divided scanning range.
Figure 3B:
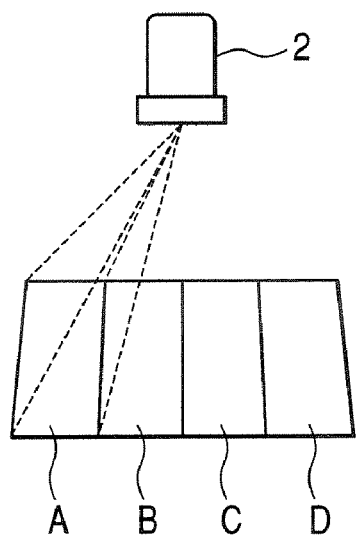
Figure 4A:
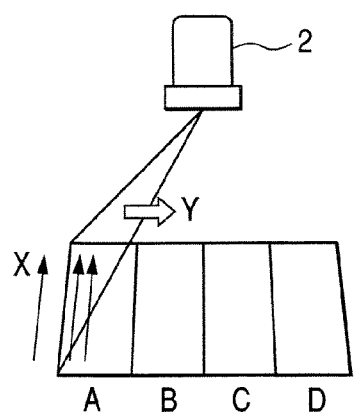
FIG. 4A is a schematic view showing a scanning range of the apparatus for obtaining an ultrasonic image according to the related art.
Figure 4B:
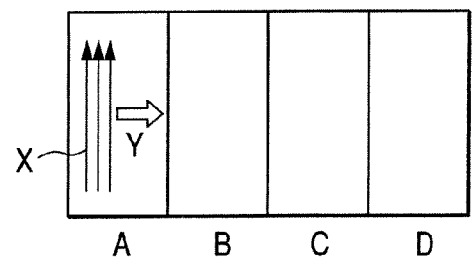
FIGS. 4B to 4D are schematic views illustrating the scanning range and scanning direction of the apparatus for obtaining an ultrasonic image according to the related art, and are diagrams (top views) seen from an ultrasonic probe.
Figure 4C:
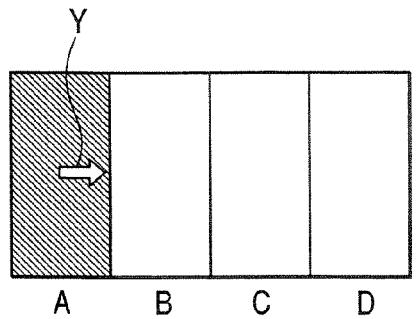
Figure 4D:
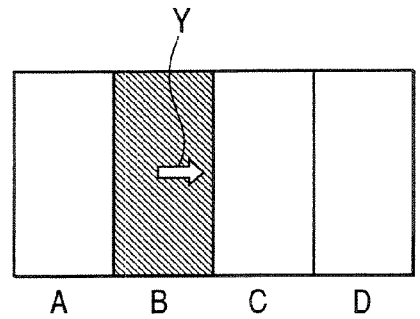
Figure 5:
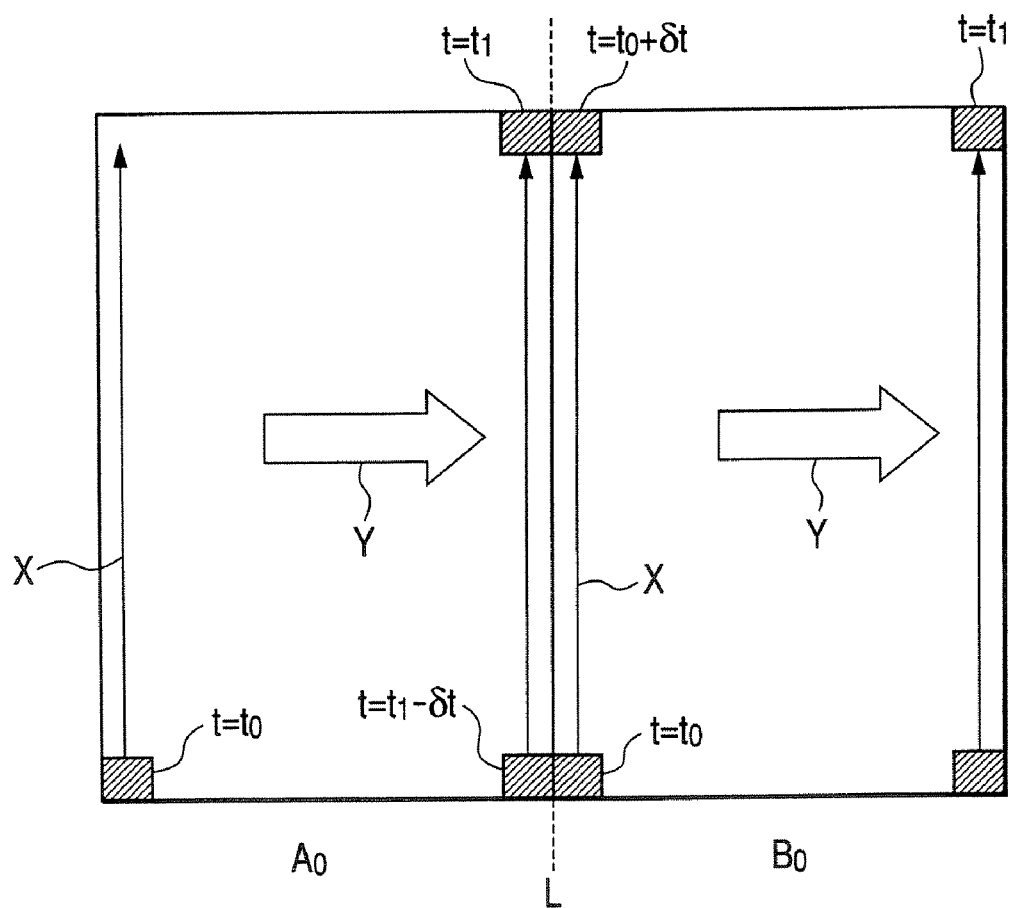
FIG. 5 is a schematic view illustrating the scanning range and scanning direction of the apparatus for obtaining an ultrasonic image according to the related art, and is a diagram (top view) seen from the ultrasonic probe.
Figure 6A:
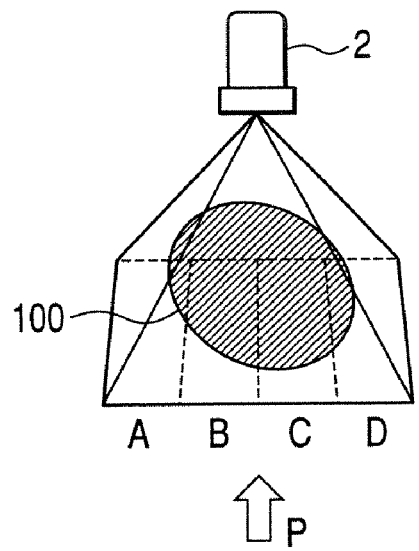
FIG. 6A is a schematic view showing a scanning range of the apparatus for obtaining an ultrasonic image according to the related art.
Figure 6B:
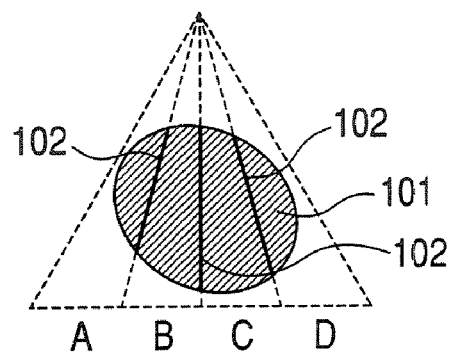
FIG. 6B is a diagram showing an image obtained by the scanning performed by the apparatus for obtaining an ultrasonic image according to the related art.

As shown in FIG. 3A, the apparatus 1 for obtaining an ultrasonic image according to the present embodiment divides the entire scanning range S into four sub-volumes A to D. As shown in FIG. 3B, the apparatus 1 for obtaining an ultrasonic image scans an ultrasonic beam by the sub-volume.

The apparatus 1 for obtaining an ultrasonic image according to the present embodiment equally divides the entire scanning range S into the sub-volumes A to D, so that the sub-volumes line up in order of A to D. Accordingly, the sub-volume B is positioned next to the sub-volume A, the sub-volume C is positioned next to the sub-volume B, that is, opposite to the sub-volume A, and the-sub-volume D is positioned next to the sub-volume C, that is, opposite to the sub-volume B. The apparatus 1 for obtaining an ultrasonic image according to the present embodiment performs scanning in order of the sub-volumes A to D.

Next, the scanning start timing will be described with reference to FIG. 8. In the present embodiment, an electrocardiographic waveform (ECG signal) of a subject is obtained by an electrocardiograph. Further, for example, when an R wave is detected by the electrocardiograph, an ECG trigger signal is generated and output to the control device 10. When the control device 10 receives the ECG trigger signal, the transmitting/receiving circuit 3 drives the ultrasonic probe 2 so as to start scanning.

When scanning is performed by using an ECG trigger signal, if the control device 10 receives a first ECG trigger signal $I_1$, the transmitting/receiving circuit 3 starts scanning in accordance with the first ECG trigger signal $I_1$. Further, at a heartbeat corresponding to the first ECG trigger signal $I_1$, the transmitting/receiving circuit 3 causes the ultrasonic probe 2 to scan the sub-volume A. For example, the transmitting/receiving circuit 3 scans the same sub-volume four times during one heartbeat so as to obtain scan data of which the time phases differ.

When the first ECG trigger signal $I_1$ is output to the control signal 10 so that the control device 10 receives the first ECG trigger signal $I_1$, the control device 10 outputs a control signal, such as delay pattern information which is required for forming a beam, to the transmitting/receiving circuit 3. The control signal includes information such as a division pattern of scanning range, the regions of sub-volumes, the main and sub-scanning directions of an ultrasonic beam. Specifically, in order to scan the sub-volume A at a heartbeat corresponding to the first ECG trigger signal $I_1$, the control device 10 outputs a control signal to the transmitting/receiving circuit 3. The control signal includes information indicating the region of the sub-volume A. The transmitting/receiving circuit 3 receives the control signal, scans the sub-volume A in accordance with the control signal so as to obtain scan data in the sub-volume A.

Here, a scanning time, which is required for scanning a sub-volume one time, is set to $\Delta t$. A time phase where the control device 10 receives the first ECG trigger signal $I_1$ is set to $t_0$, and scan data obtained when the transmitting/receiving circuit 3 starts scanning at the time phase to is set to scan data $A_0$. Further, after the transmitting/receiving circuit 3 obtains the scan data $A_0$, scan data obtained when the transmitting/receiving circuit scans at a time phase $t_1$ is set to scan data $A_1$. After the transmitting/receiving circuit 3 obtains the scan data $A_1$, scan data obtained when the transmitting/receiving circuit 3 starts scanning at a time phase $t_2$ is set to scan data $A_2$. Further, after the transmitting/receiving circuit 3 obtains the scan data $A_2$, scan data obtained when the transmitting/receiving circuit 3 starts scanning at a time phase $t_3$ is set to scan data $A_3$.

In other words, between the time phases $t_0$ and $t_1$ ($\Delta t$), the apparatus 1 for obtaining an ultrasonic image obtains the scan data $A_0$. Between the time phases $t_1$ to $t_2$ ($\Delta t$), the apparatus 1 for obtaining an ultrasonic image obtains the scan data $A_1$. Between the time phases $t_2$ to $t_3$ ($\Delta t$), the apparatus 1 for obtaining an ultrasonic image obtains the scan data $A_2$. Between the time phases $t_3$ to $t_4$ ($\Delta t$), the apparatus 1 for obtaining an ultrasonic image obtains the scan data $A_3$. As such, the apparatus 1 for obtaining an ultrasonic image obtains the scan data $A_0$ to $A_3$ during one heartbeat corresponding to the first ECG trigger signal $I_1$.

At a heartbeat corresponding to a second ECG trigger signal $I_2$, the transmitting/receiving circuit 3 scans the sub-volume B so as to obtain scan data $B_0$ to $B_3$ at the respective time phases. At a heartbeat corresponding to a third ECG trigger signal $I_3$, the transmitting/receiving circuit 3 scans the sub-volume C so as to obtain scan data $C_0$ to $C_3$ at the respective time phases. Further, at a heartbeat corresponding to a fourth ECG trigger signal $I_4$, the transmitting/receiving circuit 3 scans the sub-volume D so as to obtain scan data $D_0$ to $D_3$ at the respective time phases.

The image processor 8 combines the scan data, obtained at different heartbeats and obtained at the same time phase, so as to generate one volume data corresponding to the entire scanning range. The image processor 8 generates ultrasonic image data such as three-dimensional image data on the basis of the volume data.

For example, the image processor 8 combines the scan data $A_0$, scan data $B_0$, scan data $C_0$, and scan data $D_0$, obtained between the time phases $t_0$ to $t_1$, so as to generate scan data (volume data) of the entire range of a region of interest between the time phases $t_0$ to $t_1$. The image processor 8 generates ultrasonic image data such as three-dimensional image data on the basis of the scan data (volume data). Accordingly, the three-dimensional data is generated between the time phases $t_0$ to $t_1$.

Similarly, the image processor 8 combines scan data $A_1$, scan data $B_1$, scan data $C_1$, and scan data $D_1$, obtained between the time phases $t_1$ to $t_2$, so as to generate scan data (volume data) of the entire range of a region of interest between the time phases $t_1$ to $t_2$. The image processor 8 generates ultrasonic image data such as three-dimensional image data on the basis of the scan data (volume data). Accordingly, the three-dimensional data is generated between the time phases $t_1$ to $t_2$.

Further, the image processor 8 combines scan data $A_2$, scan data $B_2$, scan data $C_2$, and scan data $D_2$, obtained between the time phases $t_2$ to $t_3$, so as to generate scan data (volume data) of the entire range of a region of interest between the time phases $t_2$ to $t_3$. The image processor 8 generates ultrasonic image data such as three-dimensional image data on the basis of the scan data (volume data). Accordingly, the three-dimensional data is generated between the time phases $t_2$ to $t_3$.

Further, the image processor 8 combines scan data $A_3$, scan data $B_3$, scan data $C_3$, and scan data $D_3$, obtained between the time phases $t_3$ to $t_4$, so as to generate scan data (volume data) of the entire range of a region of interest between the time phases $t_3$ to $t_4$. The image processor 8 generates ultrasonic image data such as three-dimensional image data on the basis of the scan data (volume data). Accordingly, the three-dimensional data is generated between the time phases $t_3$ to $t_4$.

Here, the sub-volume scanning performed by the apparatus 1 for obtaining an ultrasonic image according to the embodiment will be described with reference to FIGS. 9A to 9E and 10. FIGS. 9A to 9E are schematic views illustrating the range and direction of scanning, which is performed by the apparatus for obtaining an ultrasonic image according to the present embodiment of the invention, and are diagrams (top views) seen from the ultrasonic probe. FIG. 10 is a schematic view illustrating the direction of scanning, which is performed by the apparatus for obtaining an ultrasonic image according to the embodiment of the invention, and is a diagram (top view) seen from the ultrasonic probe.

As shown in FIGS. 9A to 9E, regions divided by dividing lines a to c are respectively set to the sub-volumes A to D. The apparatus 1 for obtaining an ultrasonic image according to the present embodiment performs scanning in a state where the scanning directions (main and sub-scanning directions), the scanning start positions, and the scanning end positions in adjacent sub-volumes are axisymmetric with the dividing lines a to c serving as symmetrical axes. As such, when scanning is performed by changing the scanning direction, the scanning start position, and the scanning end position for each sub-volume, the difference between time phases where scan data are obtained can be reduced in the vicinities of the boundary between adjacent sub-volumes. Hereinafter, the scanning direction and the like in each of the sub-volumes will be described in detail.

Figure 9A:
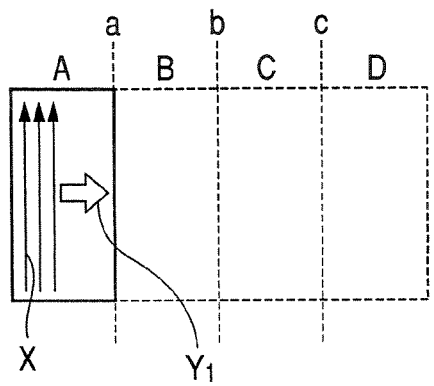
FIGS. 9A to 9E are schematic views illustrating the scanning range and scanning direction of the apparatus for obtaining an ultrasonic image according to the embodiment of the invention, and are diagrams (top views) seen from an ultrasonic probe.
Figure 10:
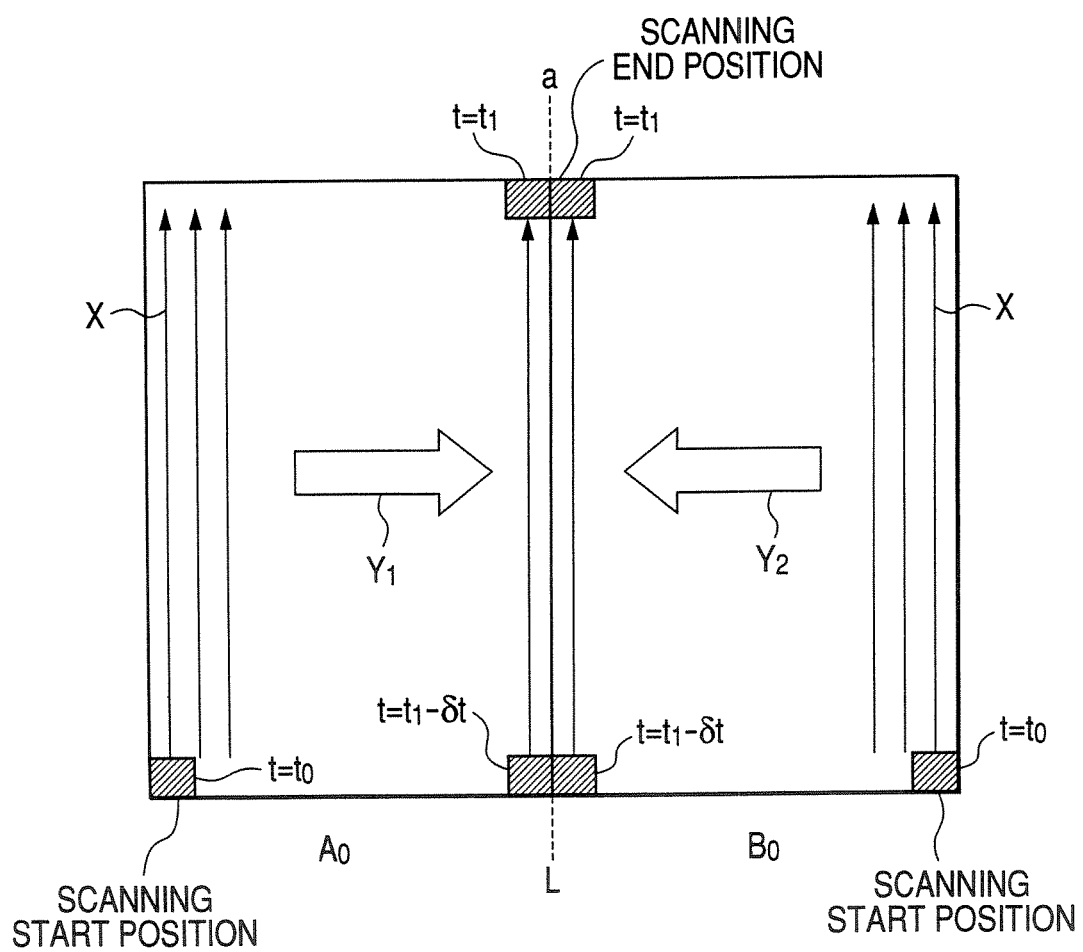
FIG. 10 is a schematic view illustrating the scanning direction of the apparatus for obtaining an ultrasonic image according to the embodiment of the invention, and is a diagram (top view) seen from the ultrasonic probe.

FIG. 9A shows a scanning direction when the sub-volume A is scanned. As shown in FIG. 9A, the transmitting/receiving circuit 3 scans an ultrasonic beam in a main scanning direction X. Further, in a state where the direction orthogonal to the main scanning direction X is set to a sub-scanning direction $Y_1$, the transmitting/receiving circuit 3 performs scanning in the sub-scanning direction $Y_1$ (from the left side to the right side in the drawing), thereby scanning the sub-volume A. That is, in the sub-volume A, the transmitting/receiving circuit 3 performs scanning toward the boundary with the adjacent sub-volume B. Further, the transmitting/receiving circuit 3 scans the sub-volume A several times (for example, four times) during one heartbeat, thereby obtaining the scan data $A_0$ to $A_3$.

Here, a representative example of the main scanning direction X will be described. In the present embodiment, for example, the transmitting/receiving circuit 3 scans an ultrasonic beam in a state where the main scanning direction X is set to the same direction for each slice, as shown in FIG. 9A. Further, as another scanning method, the transmitting/receiving circuit 3 may scan an ultrasonic beam in a state where the main scanning direction X is changed into the reverse direction for each slice, as shown in FIG. 9E. As such, any direction may be adopted as the main scanning direction X.

Hereinafter, as shown in FIG. 9A, it is assumed that the transmitting/receiving circuit 3 performs scanning in a state where the main scanning direction X of each slice is set to the same direction.

After one heartbeat, the next ECG trigger signal $I_2$ is output to the control device 10. Then, the control device 10 outputs a control signal to the transmitting/receiving circuit 3 in accordance with the ECG trigger signal $I_2$. The control signal includes information indicating the region of the sub-volume B and the main and sub-scanning directions. In accordance with the control signal, the transmitting/receiving circuit 3 transmits and receives an ultrasonic beam through the ultrasonic probe 2 so as to scan the sub-volume B.

Figure 9B:
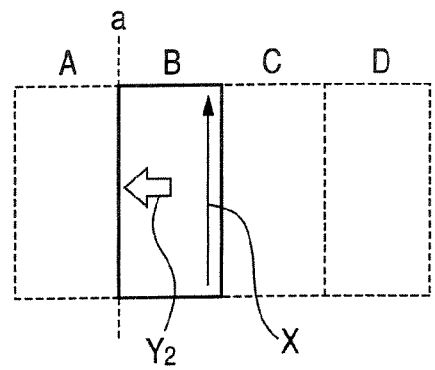

As shown in FIG. 9B, the transmitting/receiving circuit 3 scans the sub-volume B at one heartbeat, in accordance with the ECG trigger signal $I_2$. When scanning the sub-volume B, the transmitting/receiving circuit 3 performs scanning in the same direction as the main scanning direction X of the sub-volume A, in terms of a main scanning direction. In terms of a sub-scanning direction, however, the transmitting/receiving circuit 3 performs scanning in a different direction from the sub-scanning direction of the sub-volume A.

When scanning the sub-volume B, the transmitting/receiving circuit 3 scans the entire sub-volume B by scanning an ultrasonic beam in a sub-scanning direction $Y_2$ (from the left side to the right side in the drawing) which is reverse to the sub-scanning direction $Y_1$ in the sub-volume A. That is, in the sub-volume B, the transmitting/receiving circuit 3 starts scanning from the boundary with the adjacent sub-volume C so as to perform scanning toward the boundary with the adjacent sub-volume A. Further, the transmitting/receiving circuit 3 scans the sub-volume B four times during one heartbeat, thereby obtaining the scan data $B_0$ to $B_3$. As such, the control device 10 outputs a control signal including information indicating the sub-scanning direction $Y_2$ to the transmitting/receiving circuit 3, so that the transmitting/receiving circuit 3 performs scanning with the sub-scanning direction being set to be reverse.

As described above, the transmitting/receiving circuit 3 causes the ultrasonic probe 2 to scan the sub-volume B under the control of the control device 10, in a state where the scanning direction, the scanning start position, and the scanning end position in the sub-volume B adjacent to the sub-volume A are axisymmetric with the scanning direction, the scanning start position, and the scanning end position in the sub-volume A, with the dividing line set to a symmetric axis.

After one heartbeat, the next ECG trigger signal $I_3$ is output to the control device 10. Then, the control device 10 outputs a control signal to the transmitting/receiving circuit 3 in accordance with the ECG trigger signal $I_3$. The control signal includes information indicating the region of the sub-volume C and the main and sub-scanning directions. The transmitting/receiving circuit 3 transmits and receives an ultrasonic beam through the ultrasonic probe 2 in accordance with the control signal so as to scan the sub-volume C.

Figure 9C:
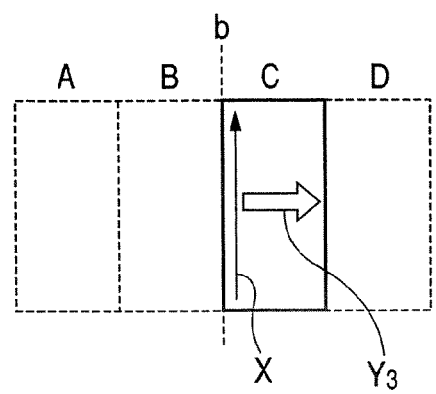

As shown in FIG. 9C, the transmitting/receiving circuit 3 scans the sub-volume C at one heartbeat in accordance with the ECG trigger signal $I_3$. When scanning the sub-volume C, the transmitting/receiving circuit 3 performs scanning in the same direction as the main scanning direction X of the sub-volume B, in terms of a main scanning direction. In terms of a sub-scanning direction, however, the transmitting/receiving circuit 3 performs scanning in a different direction from the sub-scanning direction of the sub-volume B.

When scanning the sub-volume C, the transmitting/receiving circuit 3 scans the entire sub-volume C in a sub-scanning direction $Y_3$ (from the left side to the right side in the drawing) which is reverse to the sub-scanning direction $Y_2$ in the sub-volume B. That is, in the sub-volume C, the transmitting/receiving circuit 3 starts scanning from the boundary with the adjacent sub-volume B so as to perform scanning toward the boundary with the adjacent sub-volume C. The sub-scanning direction $Y_3$ is the same direction as the sub-scanning direction $Y_1$ in the sub-volume A. Further, the transmitting/receiving circuit 3 scans the sub-volume C four times during one heartbeat, thereby obtaining the scan data $C_0$ to $C_3$. As such, the control device 10 outputs a control signal including information indicating the sub-scanning direction $Y_3$ to the transmitting/receiving circuit 3 so that the transmitting/receiving circuit 3 performs scanning in a state where the sub-scanning direction is set to be reverse.

As described above, the transmitting/receiving circuit 3 causes the ultrasonic probe 2 to scan the sub-volume C under the control of the control device 10, in a state where the scanning direction, the scanning start position, and the scanning end position in the sub-volume C adjacent to the sub-volume B are axisymmetric with the scanning direction, the scanning start position, and the scanning end position in the sub-volume B, with the dividing line serving as a symmetric axis.

After one heartbeat, the next ECG trigger signal $I_4$ is output to the control device 10. Then, the control device 10 outputs a control signal to the transmitting/receiving circuit 3 in accordance with the ECG trigger signal $I_4$. The control signal includes information indicating the region of the sub-volume D and the main and sub-scanning directions. The transmitting/receiving circuit 3 transmits and receives an ultrasonic beam through the ultrasonic probe 2 in accordance with the control signal so as to scan the sub-volume D.

Figure 9D:
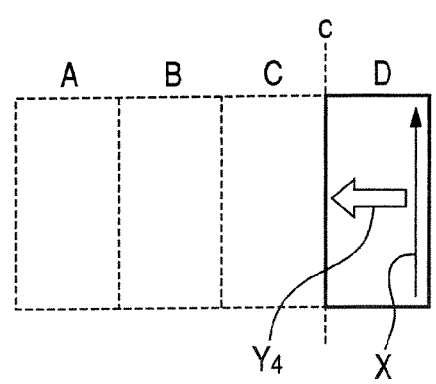
Figure 9E:
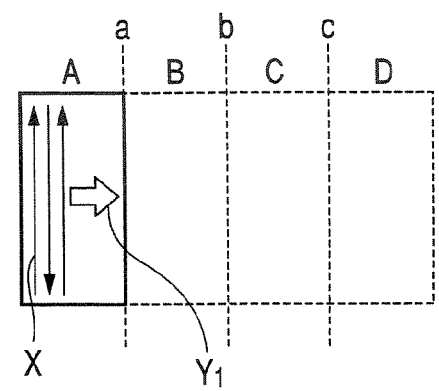

As shown in FIG. 9D, the transmitting/receiving circuit 3 scans the sub-volume D during one heartbeat in accordance with the ECG trigger signal $I_4$. When scanning the sub-volume D, the transmitting/receiving circuit 3 performs scanning in the same direction as the main scanning direction X of the sub-volume C, in terms of a main scanning direction. In terms of a sub-scanning direction, however, the transmitting/receiving circuit 3 performs scanning in a different direction from the sub-scanning direction of the sub-volume C.

When scanning the sub-volume D, the transmitting/receiving circuit 3 scans the entire sub-volume D by radiating an ultrasonic beam in a sub-scanning direction $Y_4$ (from the right side to the left side in the drawing) which is reverse to the sub-scanning direction $Y_3$ in the sub-volume C. That is, in the sub-volume D, the transmitting/receiving circuit 3 performs scanning toward the boundary with the adjacent sub-volume C. The sub-scanning direction $Y_4$ is the same direction as the sub-scanning direction $Y_2$ in the sub-volume B. Further, the transmitting/receiving circuit 3 scans the sub-volume D four times during one heartbeat, thereby obtaining the scan data $D_0$ to $D_3$. As such, the control device 10 outputs a control signal including information indicating the sub-scanning direction $Y_4$ to the transmitting/receiving circuit 3 so that the transmitting/receiving circuit 3 performs scanning with the sub-scanning direction being set to be reverse.

As described above, the transmitting/receiving circuit 3 causes the ultrasonic probe 2 to scan the sub-volume D under the control of the control device 10, in a state where the scanning direction, the scanning start position, and the scanning end position in the sub-volume D adjacent to the sub-volume C are axisymmetric with the scanning direction, the scanning start position, and the scanning end position in the sub-volume C, with the dividing line c set to a symmetric axis.

As described above, in the sub-volumes adjacent to each other, the transmitting/receiving circuit 3 performs scanning in the sub-scanning directions set to be reverse to each other. In other words, the control device 10 changes the sub-scanning direction into the reverse direction so as to set to a new sub-scanning direction, whenever an ECG trigger signal is received. Then, the control device 10 outputs a control signal to the transmitting/receiving circuit 3. The control signal includes information indicating the new sub-scanning direction. As the transmitting/receiving circuit 3 scans the sub volume in accordance with the control signal, scanning in the adjacent sub-volumes is performed in the sub-scanning directions set to be reverse to each other.

As described above, the image processor 8 serving as an image generating device combines the scan data obtained at different heartbeats, that is, the scan data obtained at the same time phase so as to generate one volume data corresponding to the entire scanning range.

For example, the image processor 8 combines the scan data $A_0$ to $D_0$ obtained between the time phases $t_0$ and $t_1$, so as to generate the scan data (volume data) of the entire range of a region of interest between the time phases $t_0$ and $t_1$, as shown in FIG. 8. Similarly, the image processor 8 combines the scan data obtained in other time phases so as to generate the scan data (volume data) of the entire range of a region of interest. Further, the image processor 8 generates ultrasonic image data such as three-dimensional image data on the basis of the scan data (volume data).

FIG. 10 shows a portion of the scan data generated in such a manner. For a simple description, only the scan data $A_0$ and $B_0$ are shown in FIG. 10. In terms of a main scanning direction, the transmitting/receiving circuit 3 scans the sub volumes A and B along the same main scanning direction X. In a sub-scanning direction, however, the transmitting/receiving circuit 3 scans the sub-volume A along the sub-scanning direction $Y_1$ and scans the sub-volume B along the sub-scanning direction $Y_2$ which is reverse to the sub-scanning direction $Y_1$.

Here, attention is paid to the vicinities of the boundary L between the sub-volumes A and B. One line of scan data obtained in a scanning range (the vicinity of the boundary L with the sub-volume B) of the right end of the sub-volume A is data obtained between time phases $(t_1-\delta t)$ to $t_1$. Meanwhile, one line of scan data obtained in a scanning range (the vicinity of the boundary L with the sub-volume A) of the left end of the sub-volume B is also data obtained between time phases $(t_1-\delta t)$ to $t_1$. Here, $\delta t$ means a time required for scanning one line, when an ultrasonic wave is scanned in the main scanning direction X. Accordingly, in the vicinities of the boundary L between the sub-volumes A and B, the time phase where the scan data $A_0$ is obtained coincides with the time phase where the scan data $B_0$ is obtained. Further, since the main scanning directions X are the same as each other, the time phases coincide with each other in the vicinities of the boundary L. Moreover, when scanning is performed in the vicinities of the boundary L in a state where the main scanning directions are set to be reverse to each other, a time phase difference as much as $\delta t$ occurs between the time phase where the scan data $A_0$ is obtained and the time phase where the scan data $B_0$ is obtained.

Even in the sub-volumes B and C and in the sub-volume C and D, scanning is performed in a state where the sub-scanning directions are set to be reverse to each other. Therefore, the difference between the time phases where the scan data are obtained can be reduced in the vicinities of the boundary between the sub-volumes.

Even on the scan data obtained between the time phases $t_1$ and $t_2$, the scan data obtained between the time phases $t_2$ and $t_3$, and the scan data obtained between the time phases $t_3$ and $t_4$, scanning in the adjacent sub-volumes is performed in a state where the sub-scanning directions set to be reverse to each other. Therefore, the difference between the time phases where the scan data are obtained can be reduced in the vicinities of the boundary between the respective sub-volumes.

As described above, the apparatus 1 for obtaining an ultrasonic image according to the present embodiment performs scanning, in a state where the scanning directions of the adjacent sub-volumes are axisymmetric with each other, with the dividing line a, b, or c being set to a symmetrical axis. Then, scanning is performed in a state where the sub-scanning directions of the adjacent sub volumes are set to be reverse to each other. As a result, the difference between the time phases where the scan data are obtained can be reduced in the vicinities of the boundary between the sub-volumes. Accordingly, a streaky artifact, which can occur in a three-dimensional image or MPR image, can be suppressed from occurring.

In the respective sub-volumes, a time phase difference $\Delta t$ ($=t_1-t_0$) occurs between the scanning start position (time phase $t_0$) and the scanning end position (time phase $t_1$). However, this also occurs in the apparatus for obtaining an ultrasonic image according to the related art.

In the apparatus 1 for obtaining an ultrasonic image according to the present embodiment, the difference between the time phases where the scan data are obtained can be reduced in the vicinities of the boundary between different sub-volumes, and an artifact, which can occur in the vicinities of the boundary, can be suppressed from occurring. Therefore, it is possible to obtain a more favorable image than in the related art.

The scan data in the respective sub-volumes obtained in such a manner are output from the transmitting/receiving circuit 3 to the B-mode processing circuit 4 or the CFM processing circuit 5. Further, the B-mode processing circuit 4 or the CFM processing circuit 5 generates B-mode raster data or color raster data. The raster data is temporarily stored and held by the memory device 6.

The image processor 8 reads the raster data, stored in the memory device 6, by the proper unit, and sequentially generates ultrasonic image data such as three-dimensional image data through image processing such as rendering. Then, the image processor 8 outputs the image data to the display device 9. Accordingly, an ultrasonic image such as a three-dimensional image is displayed on the monitor screen of the display device 9.

Figure 11:
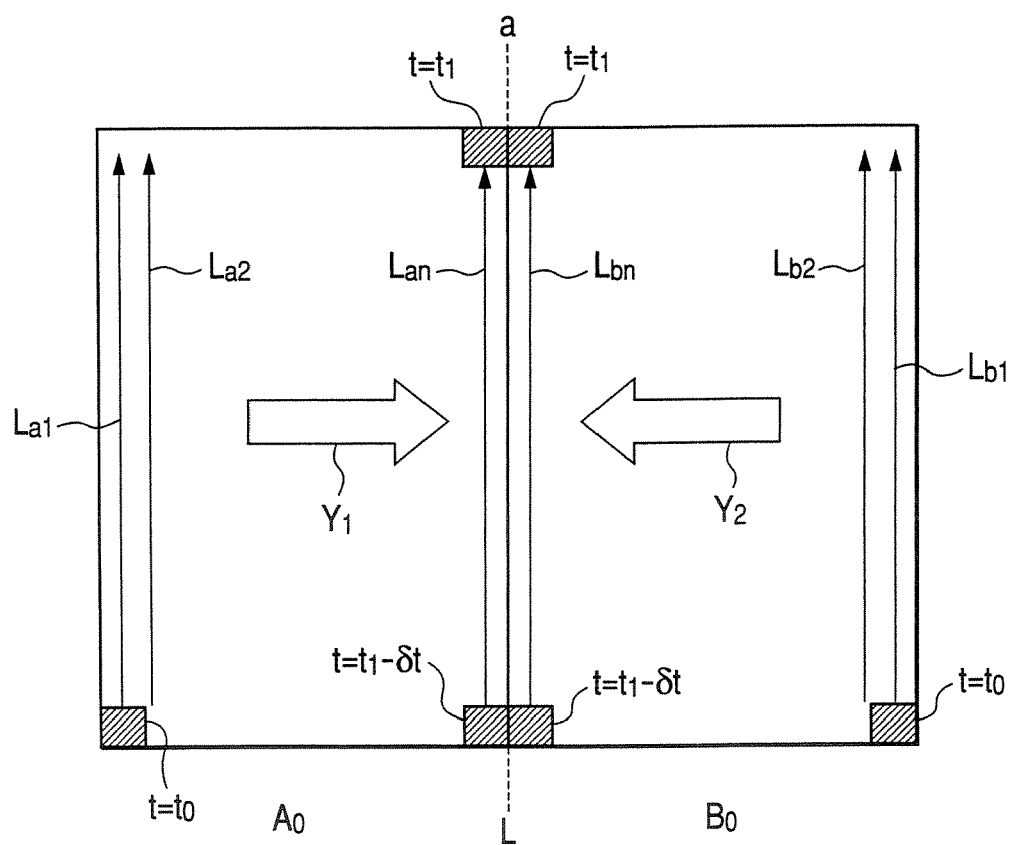
FIG. 11 is a schematic view illustrating the sequence where the scan data obtained by the apparatus for obtaining an ultrasonic image according to the embodiment of the invention are read, and is a diagram (top view) seen from the ultrasonic probe.

The sequence where the image processor 8 reads the raster data will be described with reference to FIG. 11. FIG. 11 is a schematic view illustrating an order in which the scan data obtained by the apparatus for obtaining an ultrasonic image according to the present embodiment of the invention are read, and is a diagram (top view) seen from the ultrasonic probe.

The image processor 8 reads data from the memory device 6 in accordance with the sequence of time phases where the scan data are obtained. As shown in FIG. 11, data obtained in one line is set to one unit. For the data of the sub-volume A, the image processor 8 first reads data (data obtained on a line $L_{a1}$) obtained in the earliest time phase, and second reads data (data obtained on a line $L_{a2}$) obtained in the second earliest time phase. Further, the image processor 8 also reads data, obtained after the third earliest time phase, in order according to the obtained time phases. Finally, the image process 8 reads data (data obtained on a line $L_{an}$) obtained in the n-th time phase. Accordingly, the image processor 8 reads data in order of the data obtained on the line $L_{a1}$, the data obtained on the line $L_{a2}$, . . . , the data obtained on the line $L_{an}$. That is, the image processor 8 sequentially reads the data obtained over the right end from the left end (the boundary with the sub-volume B) of the sub-volume A, the right end being the boundary with the sub-volume B.

For the sub-volume B, the image processor 8 also reads data from the memory device 6 in accordance with the sequence of time phases where the scan data are obtained. That is, the image processor 8 sequentially reads the data obtained over the left end from the right end (the boundary with the sub-volume A) of the sub-volume B, the left end being the boundary with the sub-volume A. Accordingly, the image processor 8 reads data in order of the data obtained on the line $L_{b1}$, the data obtained on the line $L_{b2}$, . . . , the data obtained on the line $L_{bn}$.

In the sub-volumes A and B, the image processor 8 sequentially reads data from the memory device 6 in the same direction as the sub-scanning direction thereof. Further, even in the sub-volumes C and D, the image processor 8 sequentially reads data from the memory device 6 in the same direction as the sub-scanning direction thereof. The image processor 8 generates ultrasonic image data such as three-dimensional data on the basis of the read data.

The above-described method of reading data may be used as it is. In the sub-volumes A and B, however, the processing load of the image processor 8 could increase, because the directions of reading data are opposite to each other and data needs to be rearranged when the image processor 8 generates three-dimensional data. Correspondingly, if data is read in order of coordinates, it is possible to reduce the processing load of the image processor 8.

For the data obtained in the sub-volume A, the image processor 8 first reads the data on the left side of the sub-volume A and sequentially reads data from the left side to the right side (the boundary with the sub-volume B). In the case of the sub-volume A, the image processor 8 reads data in accordance with the sequence of time phases where the scan data are obtained, because the direction where the image processor 8 reads data coincides with the sub-scanning direction. In FIG. 11, the image processor 8 reads data in order of the data obtained on the line $L_{a1}$, the data obtained on the line $L_{a2}$, . . . , the data obtained on the line $L_{an}$.

For the data obtained in the sub-volume B, the image processor 8 first reads the data on the left side (the boundary with the sub-volume A) of the sub-volume B, and sequentially reads data from the left side to the right side. In FIG. 11, the image processor 8 reads data in order of the data obtained on the line $L_{b1}$, the data obtained on the line $L_{b2}$, . . . , the data obtained on the line $L_{bn}$. In the case of the sub-volume B, the direction where the image processor 8 reads data is opposite to the sub-scanning direction. Therefore, the data obtained for the last time is first read, and the data obtained for the first time is lastly read. As such, as the image processor 8 reads data in order of coordinates (from the direction opposite to the sub-scanning direction), it is possible to reduce the processing load of the image processor 8 and to shorten a time required for image processing.

(Modifications)

The invention is not limited to the dividing method and the scanning direction exemplified in the above-described embodiment. A dividing method and scanning method, in which the difference between time phases where scan data are obtained does not occur in the vicinities of the boundary between adjacent sub-volumes, may be included in the scope of the invention. Although various modifications are considered as embodiments of the invention, two modifications will be described herein.

(First Modification)

Figure 12A:
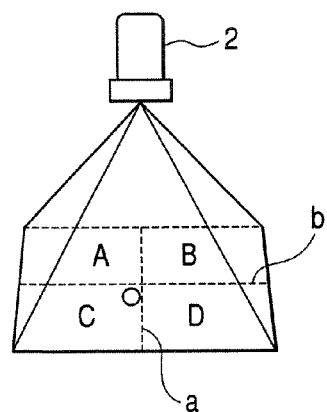
FIGS. 12A and 12B are schematic views showing a scanning range of an apparatus for obtaining an ultrasonic image according to a first modification.
Figure 12B:
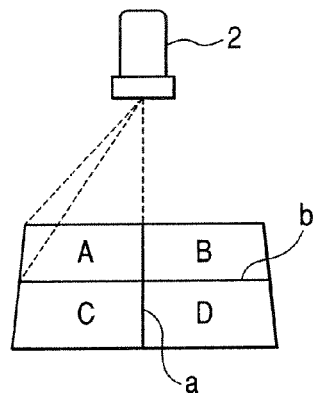

A first modification will be described with reference to FIGS. 12A to 12D. FIGS. 12A and 12B are schematic views showing a scanning range of an apparatus for obtaining an ultrasonic image according to the first modification. FIGS.

12C and 12D are schematic views illustrating the scanning range and scan direction of the apparatus for obtaining an ultrasonic image according to the first modification, and are diagram (top view) seen from the ultrasonic probe.

As shown in FIGS. 12A and 12B, the apparatus for obtaining an ultrasonic image according to the first modification equally divides the entire scanning range into four sub-volumes A to D. The apparatus 1 for obtaining an ultrasonic image according to the above-described embodiment divides the entire scanning range into four sub-volumes A to D so that the sub-volumes A to D are lined up in one line. In the apparatus for obtaining an ultrasonic image according to the first modification, however, the regions equally divided by dividing lines a and b are respectively set to the sub-volumes A to D, the dividing lines a and b passing through the center O of the entire scanning range and being orthogonal to each other.

As shown in FIG. 12B, the apparatus for obtaining an ultrasonic image according to the first modification sequentially performs scanning by the sub-volume. The scanning is performed by the control of the control device 10. The control device 10 outputs a control signal to the transmitting/receiving circuit 3, the control signal including information indicating the region of each sub-volume and the main and sub-scanning directions. In accordance with the control signal, the transmitting/receiving circuit 3 drives the ultrasonic probe 2 so as to scan each sub-volume.

Similar to the above-described embodiment, the apparatus for obtaining an ultrasonic image according to the first modification scans the sub-volume A several times (for example, four times) during a heartbeat corresponding to a first ECG trigger signal $I_1$, thereby obtaining scan data $A_0$ to $A_3$ in the respective time phases during one heartbeat. On the sub-volumes B to D, the apparatus for obtaining an ultrasonic image according to the first modification also performs scanning a plurality of times during one heartbeat so as to obtain scan data.

Figure 12C:
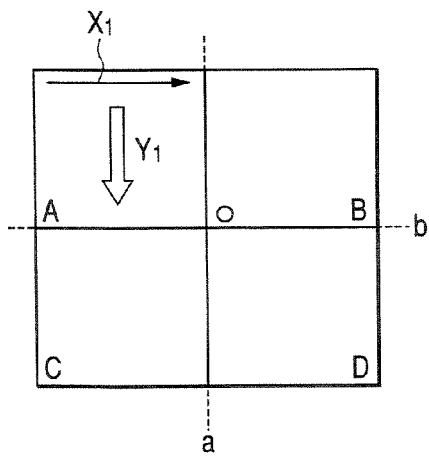
FIGS. 12C and 12D are schematic views illustrating the scanning range and scanning direction of the ultrasonic image according to the first modification, and are diagrams (top views) seen from the ultrasonic probe.
Figure 12D:
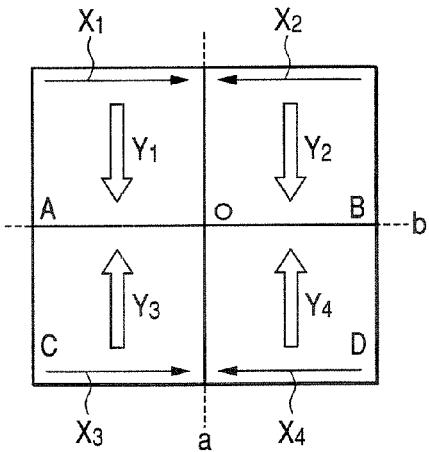

FIGS. 12C and 12D show the scanning directions of the respective sub-volumes. First, the scanning of the sub-volume A will be described. As shown in FIG. 12C, the apparatus for obtaining an ultrasonic image according to the first modification scans an ultrasonic beam in a main scanning direction $X_1$ (from the left side to the right side in the drawing) and scans an ultrasonic beam in a sub-scanning direction $Y_1$ (from the upper side to the lower side in the drawing) which is orthogonal to the main scanning direction X, thereby scanning the sub-volume A. Further, the apparatus for obtaining an ultrasonic image according to the first modification scans the sub-volume A during one heartbeat corresponding to the first ECG trigger signal $I_1$, thereby obtaining scan data $A_0$ to $A_3$.

The apparatus for obtaining an ultrasonic image according to the first modification scans the sub-volume B during one heartbeat corresponding to the next ECG trigger signal $I_2$, scans the sub-volume C during one heartbeat corresponding to the ECG trigger signal $I_3$, and scans the sub-volumes D during one heartbeat corresponding to the ECG trigger signal $I_4$. FIG. 12D shows the scanning directions of the sub-volumes A to D. The apparatus for obtaining an ultrasonic image according to the first modification scans an ultrasonic beam such that the scanning directions (the main and sub-scanning directions), the scanning start positions, and the scanning end positions in the respective sub-volumes are in an axisymmetric relationship, with the dividing line a or b set to a symmetrical axis. Accordingly, the difference between the time phases where the scanning data are obtained can be reduced in the vicinities of the boundary between the respective sub-volumes.

For example, under the control of the control device 10, the transmitting/receiving circuit 3 causes the ultrasonic probe 2 to scan the sub-volume B, in a state where the scanning direction, the scanning start position, and the scanning end position in the sub-volume B adjacent to the sub-volume A are set to be axisymmetric with the scanning direction, the scanning start position, and the scanning end position in the sub-volume A, with the dividing line a set to a symmetrical axis.

When scanning the sub-volume B, the apparatus for obtaining an ultrasonic image according to the first modification performs scanning in the same direction as the sub-scanning direction $Y_1$ of the sub-volume A, in terms of a sub-scanning direction. In terms of a main scanning direction, however, the apparatus for obtaining an ultrasonic image performs scanning in a different direction from the main scanning direction $X_1$ of the sub-volume A.

When scanning the sub-volume B, the apparatus for obtaining an ultrasonic image according to the first modification scan an ultrasonic beam in a main scanning direction $X_2$ (from the right side to the left side in the drawing) which is reverse to the main scanning direction $X_1$ in the sub-volume A. In terms of a sub-scanning direction, the apparatus for obtaining an ultrasonic image according to the first modification scans an ultrasonic beam in a sub-scanning direction $Y_2$ (from the upper side to the lower side in the drawing) so as to scan the sub-volume B, similar to the case when the sub-volume A is scanned. Accordingly, since the time phases where the scanning data are obtained substantially coincide in the vicinities of the boundary between the sub-volumes A and B, the difference between the time phases can be suppressed from occurring.

Under the control of the control device 10, the transmitting/receiving circuit 3 causes the ultrasonic probe 2 to scan the sub-volume C, in a state where the scanning direction, the scanning start position, and the scanning end position in the sub-volume C adjacent to the sub-volume A are set to be axisymmetric with the scanning direction, the scanning start position, and the scanning end position in the sub-volume A, with the diving line b set to a symmetrical axis.

When scanning the sub-volume C, the apparatus for obtaining an ultrasonic image according to the first modification scans the sub-volume C in a sub-scanning direction $Y_3$ which is reverse to the sub-scanning direction $Y_1$ in the sub-volume A, in terms of the sub-scanning direction. That is, the apparatus for obtaining an ultrasonic image according to the first modification performs scanning, in a state where the direction from the separated position to the boundary is set to the sub-scanning direction. Accordingly, since the time phases where the scan data are obtained substantially coincide in the vicinity of the boundary between the sub-volumes A and C, a time phase difference can be suppressed from occurring.

Under the control of the control device 10, the transmitting/receiving circuit 3 causes the ultrasonic probe 2 to scan the sub-volume D, in a state where the scanning direction, the scanning start position, and the scanning end position in the sub-volume D are set to be axisymmetric with the scanning direction, the scanning start position, and the scanning end position in the sub-volume B, with the diving line b set to a symmetrical axis. At this time, the scanning direction, the scanning start position, and the scanning end position in the sub-volume D are in an axisymmetric relationship with the scanning direction, the scanning start position, and the scanning end position in the sub-volume C, with the dividing line a set to a symmetric axis.

When scanning the sub-volume D, the apparatus for obtaining an ultrasonic image according to the first modification scans the sub-volume D in a sub-scanning direction $Y_4$ which is reverse to the sub-scanning direction $Y_2$ in the sub-volume B, in terms of a sub-scanning direction. That is, the apparatus for obtaining an ultrasonic image according to the first modification performs scanning, in a state where the direction from the separated position to the boundary is set to the sub-scanning direction. Accordingly, since the time phases where the scan data are obtained substantially coincide in the vicinities of the boundary between the sub-volumes B and D, a time phase difference can be suppressed from occurring.

In the relationship with the sub-volume C, the apparatus for obtaining an ultrasonic image according to the first modification scans the sub-volume D, in a state where the same direction as the sub-scanning direction in the sub-volume C is set to a sub-scanning direction and the direction reverse to the main scanning direction in the sub-volume C is set to a main scanning direction. Accordingly, since the time phases where the scan data are obtained substantially coincide in the vicinities of the boundary between the sub-volumes C and D, a time phase difference can be suppressed from occurring.

As described above, the scanning is performed by changing the main scanning directions or the sub-scanning directions of the respective sub-volumes so that the scanning directions are axisymmetric with each other. Therefore, in the vicinities of the boundary between the sub-volumes, the difference between the time phases where the scan data are obtained can be reduced. As a result, it is possible to suppress a streaky artifact from occurring in the boundary between the sub-volumes.

Second Embodiment

Figure 13A:
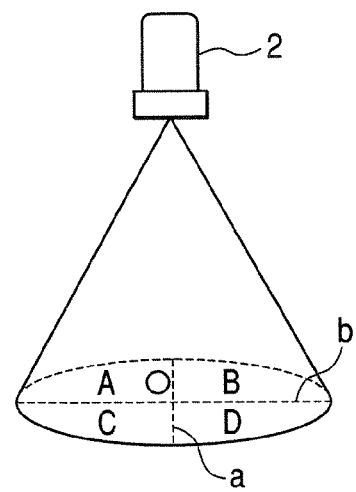
FIGS. 13A and 13B are schematic views showing a scanning range of an apparatus for obtaining an ultrasonic image according to a second modification.
Figure 13B:
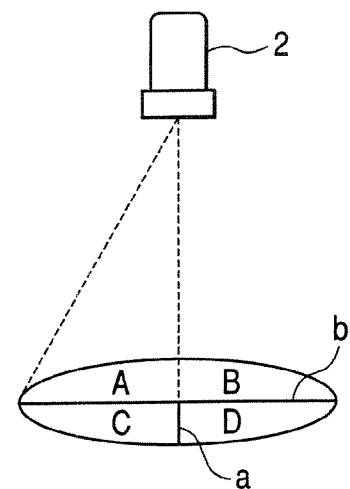
Figure 13C:
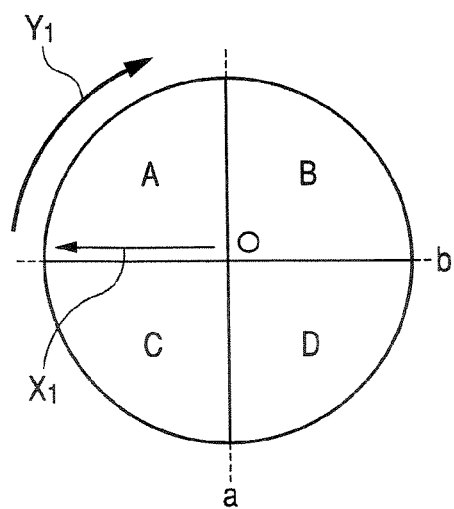
FIGS. 13C and 13D are schematic views illustrating the scanning range and scanning direction of the apparatus for obtaining an ultrasonic image according to the second modification, and are diagrams (top views) seen from the ultrasonic probe.
Figure 13D:
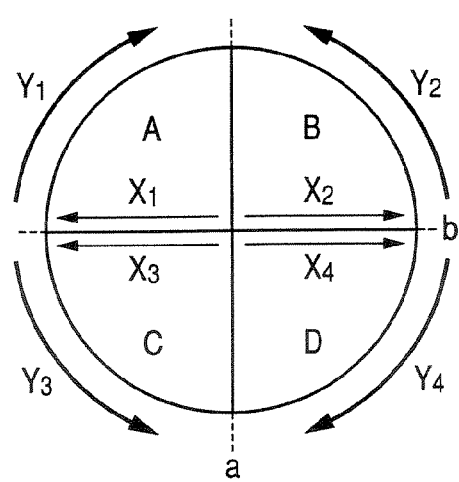

Next, a second modification will be described with reference to FIGS. 13A to 13D. FIGS. 13A and 13B are schematic views showing a region scanned by an apparatus for obtaining an ultrasonic image according to the second modification. FIGS. 13C and 13D are schematic views illustrating the region scanned by the apparatus for obtaining an ultrasonic image according to the second modification and the scanning direction thereof, and are diagrams (top views) seen from the ultrasonic probe.

As shown in FIGS. 13A and 13B, the apparatus for obtaining an ultrasonic image according to the second modification scans an ultrasonic beam, with a circular conic region set to the scan region. Further, in the apparatus for obtaining an ultrasonic image according to the second embodiment, the regions equally-divided by dividing lines a and b are respectively set to the sub-volumes A to D, the dividing lines a and b passing through the center O of the circular conic scanning range and being orthogonal to each other.

As shown in FIG. 13B, the apparatus for obtaining an ultrasonic image according to the second modification sequentially performs scanning by the sub-volume in accordance with an ECG trigger signal, thereby obtaining scan data in each time phase.

FIGS. 13C and 13D show the scanning directions of the respective sub-volumes. First, the scanning of the sub-volume A will be described. As shown in FIG. 13C, the apparatus for obtaining an ultrasonic image according to the second modification scans an ultrasonic beam in a main scanning direction $X_1$ (the radius direction in the drawing) and further scans an ultrasonic beam in a sub-scanning direction $Y_1$ (the circumferential direction), thereby scanning the sub-volume A. Further, the apparatus for obtaining an ultrasonic image according to the second modification scans the sub-volume A during one heartbeat corresponding to a first ECG trigger signal $I_1$, thereby obtaining scan data $A_0$ to $A_3$.

The apparatus for obtaining an ultrasonic image according to the second modification scans the sub-volume B during one heartbeat corresponding to the next ECG trigger signal $I_2$, scans the sub-volume C during one heartbeat corresponding to an ECG trigger signal $I_3$, and scans the sub-volume D during one heartbeat corresponding to an ECG trigger signal $I_4$. FIG. 13D shows the scanning directions of the sub-volumes A to D. The apparatus for obtaining an ultrasonic image according to the second modification scans an ultrasonic beam such that the scanning directions, the scanning start positions, and the scanning end positions in the respective sub volumes are in an axisymmetric relationship, with the dividing line a or b set to a symmetrical axis. Accordingly, in the vicinities of the boundary between the respective sub-volumes, the difference between the time phases where the scan data are obtained can be reduced.

For example, under the control of the control device 10, the transmitting/receiving circuit 3 causes the ultrasonic probe 2 to scan the sub-volume B, in a state where the scanning direction, the scanning start position, and the scanning end position in the sub-volume B adjacent to the sub-volume A are set to be axisymmetric with the scanning direction, the scanning start position, and the scanning end position in the sub-volume A, with the dividing line a set to a symmetric axis.

When scanning the sub-volume B, the apparatus for obtaining an ultrasonic image according to the second modification scans the sub-volume B in a sub-scanning direction $Y_2$ reverse to the sub-scanning direction $Y_1$ in the sub-volume A, in terms of a sub-scanning direction. That is, the apparatus for obtaining an ultrasonic image according to the second modification performs scanning, in a state where the direction from the separated position to the boundary is set to the sub-scanning direction. Accordingly, in the vicinities of the boundary between the sub-volumes A and B, a time phase difference can be suppressed from occurring, because the time phases where the scan data are obtained substantially coincide with each other.

Under the control of the control device 10, the transmitting/receiving circuit 3 causes the ultrasonic probe 2 to scan the sub-volume C, in a state where the scanning direction, the scanning start position, and the scanning end position in the sub-volume C adjacent to the sub-volume A are set to be axisymmetric with the scanning direction, the scanning start position, and the scanning end position in the sub-volume A, with the dividing line b set to a symmetric axis.

When scanning the sub-volume C, the apparatus for obtaining an ultrasonic image according to the second modification scans the sub-volume C in a sub-scanning direction $Y_3$ which is reverse to the sub-scanning direction $Y_1$ in the sub-volume A, in terms of a sub-scanning direction. That is, the apparatus for obtaining an ultrasonic image according to the second modification performs scanning, in a state where the direction away from the boundary is set to the sub-scanning direction. Accordingly, in the vicinities of the boundary between the sub-volumes A and C, a time phase difference can be suppressed from occurring, because the time phases where the scan data are obtained substantially coincide with each other.

Under the control of the control device 10, the transmitting and receiving device 3 scans the sub-volume D into the ultrasonic probe 2, in a state where the scanning direction, the scanning start position, and the scanning end position in the sub-volume D are set to be axisymmetric with the scanning direction, the scanning start position, and the scanning end position in the sub-volume B, with the dividing line b set to a symmetric axis. At this time, the scanning direction, the scanning start position, and the scanning end position in the sub-volume D are in an axisymmetric relationship with the scanning direction, the scanning start position, and the scanning end position in the sub-volume C, with the dividing line a set to a symmetric axis.

When scanning the sub-volume D, the apparatus for obtaining an ultrasonic image according to the second modification scans the sub-volume D in a sub-scanning direction $Y_4$ which is reverse to the sub-scanning direction $Y_2$ in the sub-volume B, in terms of a sub-scanning direction. That is, the apparatus for obtaining an ultrasonic image according to the second modification performs scanning, in a state where the direction away from the boundary is set to the sub-scanning direction. Accordingly, in the vicinities of the boundary between the sub-volumes B and D, a time phase difference can be suppressed from occurring, because the time phases where the scan data are obtained substantially coincide with each other. In the relationship with the sub-volume C, the apparatus for obtaining an ultrasonic image according to the second modification performs scanning in a sub-scanning direction $Y_4$ which is reverse to the sub-scanning direction $Y_3$ in the sub-volume C, in terms of a sub-scanning direction. Accordingly, the apparatus for obtaining an ultrasonic image according to the second modification performs scanning, in a state where the direction from the separated position to the boundary is set to the sub-scanning direction. Accordingly, in the vicinities of the boundary between the sub-volumes C and D, the time phase difference can be suppressed from occurring, because a time phases where the scan data are obtained substantially coincide with each other.

Figure 14:
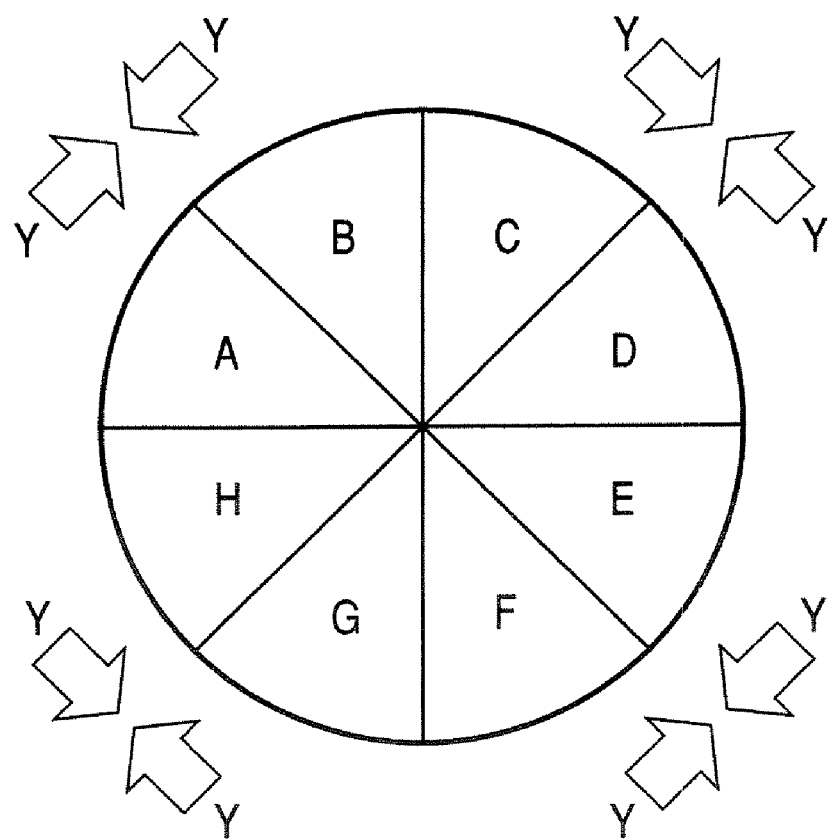
FIG. 14 is a schematic view illustrating the scanning range and scanning direction of the apparatus for obtaining an ultrasonic image according to the second modification, and is a diagram (top view) seen from the ultrasonic probe.

In the second modification, the entire scanning range has been divided into four regions. However, the scanning range may be divided into more than four regions. An example thereof will be described with reference to FIG. 14. FIG. 14 is a schematic view illustrating a scanning range and scanning direction of the apparatus for obtaining an ultrasonic image according to the second modification, and is a diagram (top view) seen from the ultrasonic probe.

As shown in FIG. 14, the entire scanning range is divided by four dividing lines which pass through the center O of the entire scanning range. Then, the entire scanning range is divided into eight regions. On the adjacent sub-volumes, the apparatus for obtaining an ultrasonic image according to the second modification performs scanning, with the sub-scanning directions Y set to be reverse to each other. Accordingly, in the vicinities of the boundary between the respective sub-volumes, a time phase difference can be reduced, because the time phases where the scan data are obtained substantially coincide. Further, the entire scanning range may be divided into $2^n$ regions (n is an integer larger than one). Even though the entire scanning range is divided into $2^n$ regions, the scanning on the adjacent sub-volumes is performed, with the sub-scanning directions set to be reverse to each other. Therefore, the difference between the time phases where the scan data are obtained can be reduced in the vicinities of the boundary.

As described above, the apparatus for obtaining an ultrasonic image according to the embodiment or modification of the invention divides a desired scanning range into a plurality of regions, and scans the respective regions in accordance with an ECG trigger signal. Therefore, although there is provided a hardware of which the parallel simultaneous reception number is small, it is possible to scan a wider region of interest.

In order to obtain the scan data in which the time phases of the electrocardiographic waveform substantially coincide with each other in the vicinities of the boundary between the respective regions, the scanning is performed by changing the main scanning direction or sub-scanning direction for each region. Then, it is possible to obtain an ultrasonic image in which a streaky artifact caused by the time phase difference is reduced. That is, the apparatus for obtaining an ultrasonic image according to the embodiment or modification of the invention scans an ultrasonic beam on the regions adjacent to each other, with the main scanning directions or sub-scanning directions set to be reverse to each other. Then, the time phases where data are obtained can be caused to coincide with each other, in the vicinity of the boundary between the regions. Therefore, the difference between the time phases where the scan data are obtained can be reduced in the vicinities of the boundary between the adjacent regions, which makes it possible to obtain an ultrasonic image in which a streaky artifact caused by the time phase difference is reduced.

What is claimed is:

1. An apparatus for obtaining an ultrasonic image comprising:
   an ultrasonic probe that scans an ultrasonic beam in a main scanning direction and a sub-scanning direction;
   a scan device that receives a trigger signal based on an electrocardiographic waveform, drives the ultrasonic probe in accordance with the trigger signal so as to scan a plurality of regions, and obtains scan data for each region; and
   an image generating device configured to combine the scan data obtained for each region so as to generate ultrasonic image data of a range in which the plurality of regions are joined,
   wherein the scan device is configured to cause the ultrasonic probe to scan the plurality of regions so that scan data in which time phases of the electrocardiographic waveform substantially coincide are obtained in the vicinities of the boundary between at least two adjacent regions among the plurality of regions, and to divide the regions by boundaries drawn extending outward from a center point of the regions in at least two directions passing through the center point.

2. The apparatus for obtaining an ultrasonic image according to claim 1,
   wherein, whenever receiving the trigger signal, the scan device causes the ultrasonic probe to scan a different region so as to obtain scan data in which the time phases of the electrocardiographic waveform substantially coincide in the vicinities of the boundary, thereby obtaining scan data for each region, and
   the image generating device combines scan data obtained by scanning the plurality of regions and the scan data obtained by starting scanning at the same time phase so as to generate ultrasonic image data of the range in which the plurality of regions are joined.

3. The apparatus for obtaining an ultrasonic image according to claim 1,
   wherein, in adjacent regions, the scan device causes the ultrasonic probe to scan the plurality of regions in the main or sub-scanning directions set to be reverse to each other so as to obtain scan data in which the time phases of the electrocardiographic waveform substantially coincide.

4. The apparatus for obtaining an ultrasonic image according to claim 1,
wherein the image generating device combines the scan data obtained by scanning the plurality of regions and the scan data obtained by starting scanning at the same time phase so as to generate ultrasonic image data of the range in which the plurality of regions are joined.

5. The apparatus for obtaining an ultrasonic image according to claim 1,
wherein, in adjacent regions among the plurality of regions, the scan device causes the ultrasonic probe to scan the plurality of regions by changing the main or sub-scanning directions so that the main or sub-scanning directions are axisymmetric with each other with a predetermined dividing line set to a symmetric axis to obtain scan data in which the time phases of the electrocardiographic waveform substantially coincide.

6. The apparatus for obtaining an ultrasonic image according to claim 1, characterized in that when the scan device drives the ultrasonic probe to scan one of the regions, the main scanning direction is axisymmetric to the main scanning direction for one of the regions adjacent to the scanned region, and the sub-scanning direction is axisymmetric to the sub-scanning direction for the other one of the regions adjacent to the scanned region.

7. The apparatus for obtaining an ultrasonic image according to claim 6, characterized in that when the scan device drives the ultrasonic probe to scan one of the regions, and the sub-scanning direction is directed to the other one of the regions adjacent to the scanned region.

8. The apparatus for obtaining an ultrasonic image according to claim 6, characterized in that when the scan device drives the ultrasonic probe to scan one of the regions, the main scanning direction is radially directed from a center, and the sub-scanning direction is circumferentially directed and opposite to the sub-scanning direction of the regions adjacent to the scanned region.

9. An apparatus for obtaining an ultrasonic image comprising:
an ultrasonic probe that scans an ultrasonic beam in a main scanning direction and a sub-scanning direction;
a scan device that receives a trigger signal based on an electrocardiographic waveform, drives the ultrasonic probe in accordance with the trigger signal so as to scan a plurality of regions, and obtains scan data for each region; and
an image generating device configured to combine the scan data obtained for each region so as to generate ultrasonic image data of a range in which the plurality of regions are joined,
wherein, in adjacent regions, the scan device is configured to cause the ultrasonic probe to scan the plurality of regions in the main or sub-scanning directions set to be reverse to each other so as to obtain scan data, and to divide the regions by boundaries drawn extending outward from a center point of the regions in at least two directions passing through the center point.

10. The apparatus for obtaining an ultrasonic image according to claim 9,
wherein, whenever receiving the trigger signal, the scan device causes the ultrasonic probe to scan a different region, and the scan device causes the ultrasonic probe to scan the plurality of regions in the main or sub-scanning directions set to be reverse to each other in adjacent regions, so as to obtain scan data, and
the image generating device combines the scan data obtained by scanning the plurality of regions and the scan data obtained by starting scanning at the same time phase, so as to generate ultrasonic image data of the range in which the plurality of regions are joined.

11. The apparatus for obtaining an ultrasonic image according to claim 9,
wherein the image generating device combines the scan data obtained by scanning the plurality of regions and the scan data obtained by starting scanning at the same time phase, so as to generate ultrasonic image data of the range in which the plurality of regions are joined.

12. The apparatus for obtaining an ultrasonic image according to claim 9,
wherein, in adjacent regions among the plurality of regions, the scan device causes the ultrasonic probe to scan the plurality of regions by changing the main or sub-scanning directions so that the main or sub-scanning directions are axisymmetric with each other with a predetermined dividing line set to a symmetric axis to obtain scan data.

13. The apparatus for obtaining an ultrasonic image according to claim 9, characterized in that when the scan device drives the ultrasonic probe to scan one of the regions, the main scanning direction is axisymmetric to the main scanning direction for one of the regions adjacent to the scanned region, and the sub-scanning direction is axisymmetric to the sub-scanning direction for the other one of the regions adjacent to the scanned region.

14. The apparatus for obtaining an ultrasonic image according to claim 13, characterized in that when the scan device drives the ultrasonic probe to scan one of the regions, and the sub-scanning direction is directed to the other one of the regions adjacent to the scanned region.

15. The apparatus for obtaining an ultrasonic image according to claim 13, characterized in that when the scan device drives the ultrasonic probe to scan one of the regions, the main scanning direction is radially directed from a center, and the sub-scanning direction is circumferentially directed and opposite to the sub-scanning direction of the regions adjacent to the scanned region.

16. A method of obtaining an ultrasonic image comprising:
obtaining scan data for each of a plurality of regions by receiving a trigger signal based on an electrocardiographic waveform, driving an ultrasonic probe in accordance with the trigger signal, and scanning the plurality of regions in a main scanning direction and a sub-scanning direction through the ultrasonic probe; and
generating ultrasonic image data of a range in which the plurality of regions are joined, by combining the scan data obtained for each region,
wherein, in the obtaining of scan data, the ultrasonic probe scans adjacent regions in the main or sub-scanning directions set to be reverse to each other so as to obtain scan data, and divides the regions by boundaries drawn extending outward from a center point of the regions in at least two directions passing through the center point.

17. The method of obtaining an ultrasonic image according to claim 16,
wherein, in the obtaining of scan data, whenever receiving the trigger signal, the ultrasonic probe scans a different region, and the ultrasonic probe scans the plurality of regions in the main or sub-scanning directions set to be reverse to each other in adjacent regions, so as to obtain scan data, and
in the generating of the ultrasonic image data, the scan data obtained by scanning the plurality of regions and the scan data obtained by starting scanning at the same time phase are combined so as to generate ultrasonic image data of the range in which the plurality of regions are joined.

18. The method of obtaining an ultrasonic image according to claim 16,
wherein, in the generating of the ultrasonic image data, the scan data obtained by scanning the plurality of regions and the scan data obtained by starting scanning at the same time phase are combined so as to generate ultrasonic image data of the range in which the plurality of regions are joined.

19. The method of obtaining an ultrasonic image according to claim 16,
wherein, in the obtaining of scan data, in adjacent regions among the plurality of regions, the ultrasonic probe scans the plurality of regions by changing the main or sub-scanning directions so that the main or sub-scanning directions are axisymmetric with a predetermined dividing line set to a symmetric axis to obtain scan data.

20. The apparatus for obtaining an ultrasonic image according to claim 16, characterized in that when the scan device drives the ultrasonic probe to scan one of the regions, the main scanning direction is axisymmetric to the main scanning direction for one of the regions adjacent to the scanned region, and the sub-scanning direction is axisymmetric to the sub-scanning direction for the other one of the regions adjacent to the scanned region.

21. The apparatus for obtaining an ultrasonic image according to claim 20, characterized in that when the scan device drives the ultrasonic probe to scan one of the regions, and the sub-scanning direction is directed to the other one of the regions adjacent to the scanned region.

22. The apparatus for obtaining an ultrasonic image according to claim 20, characterized in that when the scan device drives the ultrasonic probe to scan one of the regions, the main scanning direction is radially directed from a center, and the sub-scanning direction is circumferentially directed and opposite to the sub-scanning direction of the regions adjacent to the scanned region.

* * * * *